(12) United States Patent
Hoerstrup et al.

(10) Patent No.: US 11,946,071 B2
(45) Date of Patent: Apr. 2, 2024

(54) BIOENGINEERED IN VITRO 3D MODEL OF HUMAN ATHEROSCLEROTIC PLAQUE

(71) Applicant: UNIVERSITÄT ZÜRICH, Zürich (CH)

(72) Inventors: Simon Hoerstrup, Schlieren (CH); Benedikt Weber, Vienna (AT); Anna Mallone, Schlieren (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 816 days.

(21) Appl. No.: 16/641,137

(22) PCT Filed: Aug. 23, 2018

(86) PCT No.: PCT/EP2018/072740
§ 371 (c)(1),
(2) Date: Feb. 21, 2020

(87) PCT Pub. No.: WO2019/038363
PCT Pub. Date: Feb. 28, 2019

(65) Prior Publication Data
US 2020/0325445 A1  Oct. 15, 2020

(30) Foreign Application Priority Data
Aug. 23, 2017  (EP) .................................... 17187562

(51) Int. Cl.
| | |
|---|---|
| *C12N 5/0784* | (2010.01) |
| *C12N 5/071* | (2010.01) |
| *C12N 5/077* | (2010.01) |
| *C12N 5/0786* | (2010.01) |
| *C12Q 1/6883* | (2018.01) |
| *G01N 33/68* | (2006.01) |

(52) U.S. Cl.
CPC ......... *C12N 5/0645* (2013.01); *C12N 5/0639* (2013.01); *C12N 5/0656* (2013.01); *C12N 5/0697* (2013.01); *C12Q 1/6883* (2013.01); *G01N 33/6893* (2013.01); *C12N 2500/34* (2013.01); *C12N 2501/727* (2013.01); *C12N 2502/1323* (2013.01); *C12N 2513/00* (2013.01)

(58) Field of Classification Search
CPC .. C12N 5/0645; C12N 5/0639; C12N 5/0656; C12N 5/0697; C12N 2500/34; C12N 2501/727; C12N 2502/1323; C12N 2513/00; C12N 2500/36; C12N 2501/052; C12N 2502/11; C12N 2506/115; C12N 5/0691; C12Q 1/6883; G01N 33/6893
See application file for complete search history.

(56) References Cited

FOREIGN PATENT DOCUMENTS

WO    WO 2019/038363    2/2019

OTHER PUBLICATIONS

Dorweiler et al., "A novel in vitro model for the study of plaque development in atherosclerosis", Thrombosis and Haemostasis, vol. 95, pp. 182-189 (Year: 2006).*
Foty et al., "A simple hanging drop cell culture protocol for generation of 3D spheroids", Journal of Visualized Experiments, vol. 6, e2720, pp. 1-4 (Year: 2011).*
Dorweiler, A novel invitro model for the study of plaque development in atherosclerosis, 2006, Schattauer GmbH, New technologies, diagnostic tools and drugs. (Year: 2006).*
Foty, A simple Hanging drop cell culture protocol for generation of 3D spheroids, 2011, Jove, video article, DOI 10.3791/2720. (Year: 2011).*
PCT, PCT/EP2018/072740 (WO 2019/038363), Aug. 23, 2018 (Feb. 28, 2019), UNIVERSITÄT ZÜRICH.
Office Action dated Jul. 28, 2021 by the European Patent Office in EP Application No. 18758617.7, which was filed on Aug. 23, 2018. (Inventor—Hoerstrup) (4 pages).
Amir El, A. D., "ViSNE enables Visualization of higll dimensional single-cell data and reveals phenotypic heterogeneity of leukemia", Nat Biotechnol, vol. 31, (2013), pp. 545-552.
Aper et al: "Use of a Fibrin Preparation in the Engineering of a Vascular Graft Model", Eur J Vasc Endovasc Surg. (2004), (3):296-302.
Bartosh et al., Aggregation of human mesenchymal stromal cells (MSCs) into 3D spheroids enhances their antiinflammatory properties, Proc Natl Acad Sci U S A. (2010), 107(31):13724-9.
Bonanno et al., "Flow cytometry analysis of atherosclerotic plque cells from human carotoids: a validation study", Cytometry. (2000), 39(2): 158-65.
Mallone et al: "Biofabricating atherosclerotic plaqueszln vitroengineering of a three-dimensional human fibroatheroma model", Biomaterials, vol. 150, (2017), pp. 49-59.
Menck, K., "Isolation of Human Monocytes by Double Gradient Centrifugation and Their Differentiation to Macrophages in Teflon-coated Cell Culture Bags",J Vis Exp, (2014), pp. e51554.
Moore et al., "Macrophages in the pathogenesis of atherosclerosis", Cell. (2011), 145(3):341-55.
Randolph, "Mechanisms that regulate macrophage burden in atherosclerosis", Circ Res, (2014) 114:1757-1771.
Van Der Maaten, et al., "Visualizing Data using t-SNE", Journal of Machine Learning Research 9 (2008) 2579-2605.
Wada et al: "In vitro model of atherosclerosis using coculture of arterial wall cells and macrophage", Yonsei Med J. (2000), 41(6):740-55.

(Continued)

*Primary Examiner* — Emily A Cordas
*Assistant Examiner* — Constantina E Stavrou
(74) *Attorney, Agent, or Firm* — BALLARD SPAHR LLP

(57) ABSTRACT

The invention provides a method for the generation of a layered cellular 3 D microtissue aggregate, comprising the steps of contacting myeloid cells with a protein kinase C agonist, yielding primed myeloid cells; incubating the primed myeloid cells in the presence of LDL in a confined volume, particularly in a hanging drop culture; yielding a 3 D culture of myeloid cells; and incubating the 3 D culture together with fibroblasts in a hanging drop in the presence of LDL, yielding the layered cellular aggregate.

14 Claims, 25 Drawing Sheets
Specification includes a Sequence Listing.

(56) References Cited

OTHER PUBLICATIONS

Williams et al: "Platelets and Smooth Muscle Cells Affecting the Differentiation of Monocytes", PLOS ONE, vol. 9, No. 2, (2014), pp. e88172.
Zhang et al: "AMP-activated protein kinase α1 promotes atherogenesis by increasing monocyte-to-macrophage differentiation", Journal of Biological Chemistry, vol. 292, No. 19, (2017), US, pp. 7888-7903.
International Search Report and Written Opinion dated Oct. 19, 2018 by the International Searching Authority for International Application No. PCT/EP2018/072740, filed on Aug. 23, 2018 and published as WO/2019/038363 dated Feb. 28, 2019(Applicant— UNIVERSITÄT ZÜRICH)(10 Pages).

\* cited by examiner

Fig. 2
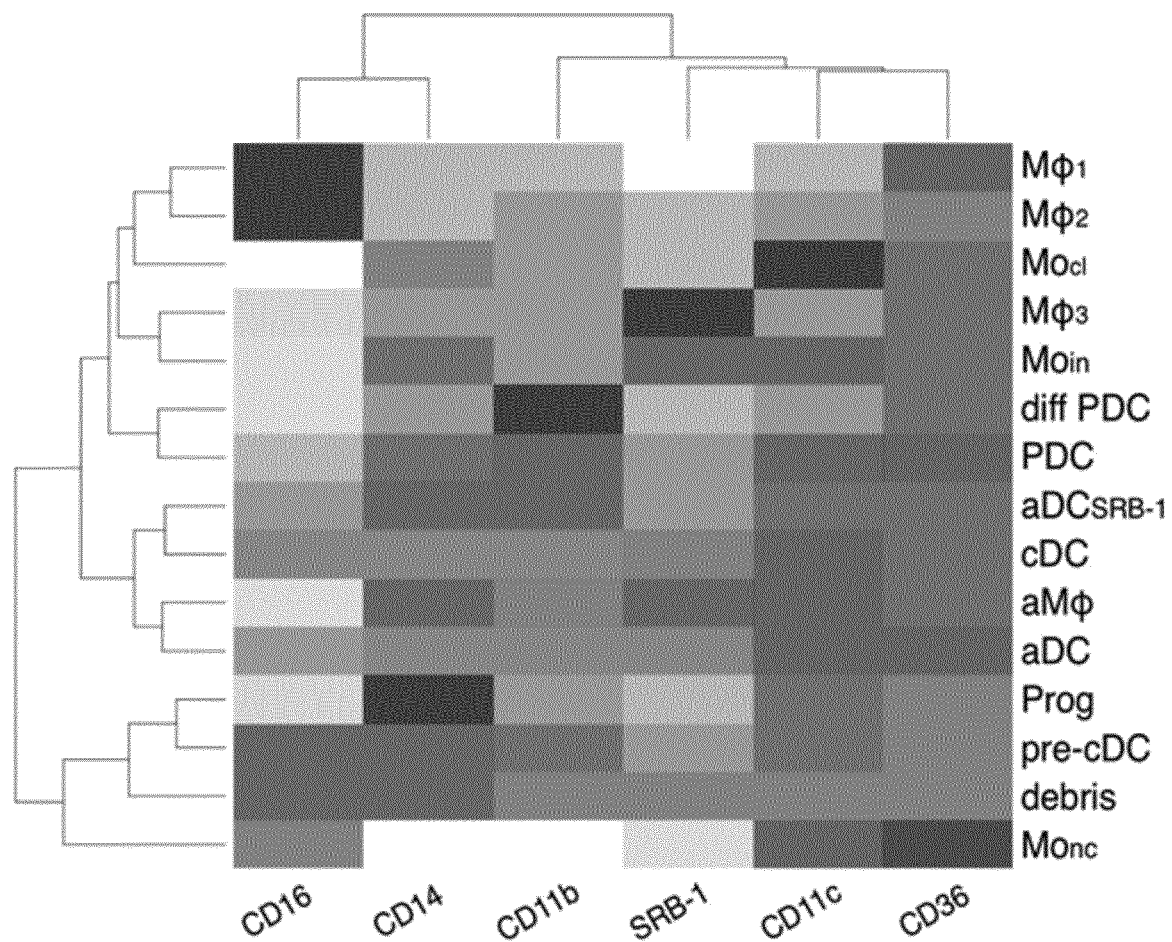
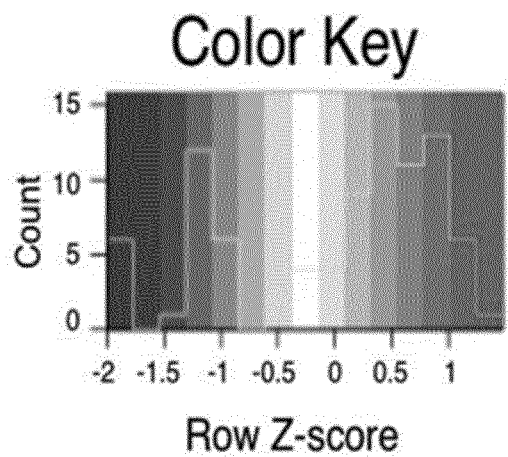

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Primer CXCL10 forward

<400> SEQUENCE: 1
gcaagccaat dtgtccacg                                              19

<210> SEQ ID NO 2
<211> LENGTH: 23
<212> TYPE: DNA
<213> ORGANISM: Artificial Sequence
<220> FEATURE:
<223> OTHER INFORMATION: CXCL10 rev

<400> SEQUENCE: 2
acadtccttg ctaactgcdt cag                                         23

<210> SEQ ID NO 3
<211> LENGTH: 26
<212> TYPE: DNA
<213> ORGANISM: Artificial Sequence
<220> FEATURE:
<223> OTHER INFORMATION: CCR7 for

<400> SEQUENCE: 3
gaaagtccag aaactgdccc acctgc                                      26

<210> SEQ ID NO 4
<211> LENGTH: 26
<212> TYPE: DNA
<213> ORGANISM: Artificial Sequence
<220> FEATURE:
<223> OTHER INFORMATION: CCR7 rev

<400> SEQUENCE: 4
cccctctgaa gaaccgaacc actccd                                      26

<210> SEQ ID NO 5
<211> LENGTH: 28
<212> TYPE: DNA
<213> ORGANISM: Artificial Sequence
<220> FEATURE:
<223> OTHER INFORMATION: CCL17 for

<400> SEQUENCE: 5
ccagggatgc catcgtddgt aactgtgc                                    28

<210> SEQ ID NO 6
<211> LENGTH: 30
<212> TYPE: DNA
<213> ORGANISM: Artificial Sequence
<220> FEATURE:
<223> OTHER INFORMATION: CCL17 rev

<400> SEQUENCE: 6
cctcactgtg gctcttcttc gtccctggaa                              30

<210> SEQ ID NO 7
<211> LENGTH: 23
<212> TYPE: DNA
<213> ORGANISM: Artificial Sequence
<220> FEATURE:
<223> OTHER INFORMATION: CCL26 for

<400> SEQUENCE: 7
gcctgadtgc agcatcatga tgg                                     23

<210> SEQ ID NO 8
<211> LENGTH: 23
<212> TYPE: DNA
<213> ORGANISM: Artificial Sequence
<220> FEATURE:
<223> OTHER INFORMATION: CCL26 rev

<400> SEQUENCE: 8
cggatgacaa dcagctgagt cac                                     23

<210> SEQ ID NO 9
<211> LENGTH: 21
<212> TYPE: DNA
<213> ORGANISM: Artificial Sequence
<220> FEATURE:
<223> OTHER INFORMATION: DC-SIGN for

<400> SEQUENCE: 9
tcgaggatac aagagcdagc a                                       21

<210> SEQ ID NO 10
<211> LENGTH: 18
<212> TYPE: DNA
<213> ORGANISM: Artificial Sequence
<220> FEATURE:
<223> OTHER INFORMATION: DC-SIGN rev

<400> SEQUENCE: 10
aaggagccca gccaagag                                           18

<210> SEQ ID NO 11
<211> LENGTH: 21
<212> TYPE: DNA
<213> ORGANISM: Artificial Sequence
<220> FEATURE:
<223> OTHER INFORMATION: IL10 for

<400> SEQUENCE: 11
ctgtgaaaac aagagcaagg c                                       21

<210> SEQ ID NO 12
<211> LENGTH: 18
<212> TYPE: DNA
<213> ORGANISM: Artificial Sequence
<220> FEATURE:

```
<223> OTHER INFORMATION: IL10 rev

<400> SEQUENCE: 12
gaagcttctg dggctccc                                              18

<210> SEQ ID NO 13
<211> LENGTH: 20
<212> TYPE: DNA
<213> ORGANISM: Artificial Sequence
<220> FEATURE:
<223> OTHER INFORMATION: IL23 for

<400> SEQUENCE: 13
gcagattcca agcctcagtc                                            20

<210> SEQ ID NO 14
<211> LENGTH: 19
<212> TYPE: DNA
<213> ORGANISM: Artificial Sequence
<220> FEATURE:
<223> OTHER INFORMATION: IL23 rev

<400> SEQUENCE: 14
dcaacatatg caggtccca                                             19

<210> SEQ ID NO 15
<211> LENGTH: 19
<212> TYPE: DNA
<213> ORGANISM: Artificial Sequence
<220> FEATURE:
<223> OTHER INFORMATION: PTGS1 for

<400> SEQUENCE: 15
cgccagtgaa tccctgdgd                                             19

<210> SEQ ID NO 16
<211> LENGTH: 20
<212> TYPE: DNA
<213> ORGANISM: Artificial Sequence
<220> FEATURE:
<223> OTHER INFORMATION: PTGS1 rev

<400> SEQUENCE: 16
aaggtggcad gacaaactcc                                            20

<210> SEQ ID NO 17
<211> LENGTH: 19
<212> TYPE: DNA
<213> ORGANISM: Artificial Sequence
<220> FEATURE:
<223> OTHER INFORMATION: CGC CGA CD TGA GAA AAT CT

<400> SEQUENCE: 17
cgccgacdtg agaaaatct                                             19

<210> SEQ ID NO 18
<211> LENGTH: 20
<212> TYPE: DNA
<213> ORGANISM: Artificial Sequence
<220> FEATURE:
<223> OTHER INFORMATION: ALOX5 rev

<400> SEQUENCE: 18
ggctgcactc taccatctcc                                            20
```

```
<210> SEQ ID NO 19
<211> LENGTH: 19
<212> TYPE: DNA
<213> ORGANISM: Artificial Sequence
<220> FEATURE:
<223> OTHER INFORMATION: SRB1 for

<400> SEQUENCE: 19
tcctcacdcc tcaacgctg                                                 19

<210> SEQ ID NO 20
<211> LENGTH: 18
<212> TYPE: DNA
<213> ORGANISM: Artificial Sequence
<220> FEATURE:
<223> OTHER INFORMATION: SRB1 rev

<400> SEQUENCE: 20
tcccagtdgt ccaatgcc                                                  18

<210> SEQ ID NO 21
<211> LENGTH: 20
<212> TYPE: DNA
<213> ORGANISM: Artificial Sequence
<220> FEATURE:
<223> OTHER INFORMATION: GAPDH for

<400> SEQUENCE: 21
gtcagtggtg gacctgacct                                                20

<210> SEQ ID NO 22
<211> LENGTH: 20
<212> TYPE: DNA
<213> ORGANISM: Artificial Sequence
<220> FEATURE:
<223> OTHER INFORMATION: GAPDH rev

<400> SEQUENCE: 22
acctggtgct cagtgtagcc                                                20

<210> SEQ ID NO 23
<211> LENGTH: 24
<212> TYPE: DNA
<213> ORGANISM: Artificial Sequence
<220> FEATURE:
<223> OTHER INFORMATION: 18S for

<400> SEQUENCE: 23
cccggggagg tagtgacgaa aaat                                           24

<210> SEQ ID NO 24
<211> LENGTH: 23
<212> TYPE: DNA
<213> ORGANISM: Artificial Sequence
<220> FEATURE:
<223> OTHER INFORMATION: 18S rev

<400> SEQUENCE: 24
gcccgctccc aagatccaac tac                                            23
```

BIOENGINEERED IN VITRO 3D MODEL OF HUMAN ATHEROSCLEROTIC PLAQUE

CROSS REFERENCE TO RELATED PATENT APPLICATIONS

This application claims the benefit of priority under 35 U.S.C. § 371 of International Application No. PCT/EP2018/072740, filed on Aug. 23, 2018, which claims the benefit of priority to European Application No. 17187562.8, filed on Aug. 23, 2017. The content of these earlier filed applications is hereby incorporated by reference.

REFERENCE TO SEQUENCE LISTING

The Sequence Listing submitted Feb. 21, 2020 as a text file named "13318_0050U1_Sequence_Listing.txt," created on Feb. 21, 2020, and having a size of 4,978 bytes is hereby incorporated by reference pursuant to 37 C.F.R. § 1.52(e)(5).

The present invention relates to the in vitro generation of a bioengineered 3D model of human late-stage atherosclerosis.

Atherosclerosis is a life threatening vascular pathology characterized by the accumulation of a fatty plaque in the vascular sub-endothelial space. Atherosclerotic plaque formation is influenced by the synergistic interplay of different risk factors such as sex, age, genetic predisposition, high blood pressure and high blood levels of low-density lipoprotein (LDL) cholesterol. The formation of a well-structured plaque microenvironment results from the interplay of cholesterol-rich lipoproteins, endothelial cells, monocytes, macrophages, dendritic cells and fibroblasts in a complex matrix milieu. The process of plaque formation is progressive and reversible and can be counteracted by a reduction of risk factors or promoted by their persistence. Plaques are classified according to their stage of development and cellular components. Among different plaque stages, the thin-cap fibroatheroma is the one most prone to rupture and to potentially cause thrombus formation and vessel obstruction. The fibroatheroma is characterized by the presence of a necrotic core, macrophage-derived foam cells and dendritic cells all being enriched with cholesterol and embedded in a collagenous matrix surrounded by a thin layer of fibrotic cells. The cellular mechanisms underlying plaque formation and regression have been investigated in vivo in both small and large animals, predominantly in hypercholesterolemic mice with knock-out of either ApoE or LDL-receptor, and in non-human primates. Despite the stunning contribution to the field, major differences in anatomy, lipoprotein profiles and inflammatory mechanisms hampered the translation of these results to the human pathophysiology. To overcome the translational gap, human cell-based co-culture in vitro models have been established and provided a first glimpse into the initial events of plaque deposition in humans. So far, no human model of late stages of atherosclerotic plaque development exists.

Based on the above-mentioned state of the art, the objective of the present invention is to provide means and methods to generate a bioengineered in vitro model of human atherosclerotic plaques, in particular fibroatheroma. This objective is attained by the subject matter of the present specification.

DESCRIPTION

Terms and Definitions

The terms "pseudo-plaque", "ps-plaque" and "bioengineered plaque" in the context of the present specification relate to the layered cellular (3 dimensional microtissue) aggregate according to the invention. The pseudo plaque serves as in vitro model of human fibroatheroma. The ps-plaque architecture is characterized by a spheroid core of monocytes, macrophages and dendritic cells embedded in a collagenous and lipid-rich matrix, surrounded by a thin layer of fibroblasts.

The term "protein kinase C agonist" in the context of the present specification relates to a compound able to activate (or increase the activity of) the enzyme protein kinase C. By way of non-limiting example, the protein kinase C agonist can be phorbol 12-myristate 13-acetate (PMA), diacylglycerin or a synthetic mimic thereof.

The term "hanging drop culture" in the context of the present specification relates to a form of tissue culture in which a drop comprising cells and media is suspended from an inverted lid of a tissue culture plate. The bottom of the plate is filled with liquid (e.g. 1×PBS) to create a humid environment necessary to keep the drop volume constant. The plates are usually kept at 37° C. and 5% $CO_2$.

In the present specification, the term positive, when used in the context of expression of a marker, refers to expression of an antigen assayed by a fluorescently labelled antibody, wherein the label's fluorescence on the structure (for example, a cell) referred to as "positive" is at least 30% higher 30%), particularly ≥50% or ≥80%, in median fluorescence intensity in comparison to staining with an isotype-matched fluorescently labelled antibody which does not specifically bind to the same target. Such expression of a marker is indicated by a superscript "plus" (k), following the name of the marker, e.g. $CD4^+$.

In the present specification, the term negative, when used in the context of expression of a marker, refers to expression of an antigen assayed by a fluorescently labelled antibody, wherein the median fluorescence intensity is less than 30% higher, particularly less than 15% higher, than the median fluorescence intensity of an isotype-matched antibody which does not specifically bind the same target. Such expression of a marker is indicated by a superscript minus (⁻) following the name of the marker, e.g. $CD127^-$.

The term "myeloid cells" in the context of the present specification relates to cells of myeloid origin which are the starting cell population in the method according the invention. The myeloid cells are provided either ex-vivo from a patient by isolation from fresh blood using a double gradient centrifugation or as cell culture or cell line characterized by expression of monocyte/macrophage cell markers.

The term "monocyte" in the context of the present specification relates to a type of white blood cell (leukocyte). Monocytes constitute between 3% to 8% of the leukocytes in the blood. They are produced by the bone marrow from precursors called monoblasts and circulate in the blood stream for about 1 to 3 days before they move into tissues throughout the body where they differentiate into macrophages and (myeloid lineage) dendritic cells.

The term "macrophage" in the context of the present specification relates to a type of white blood cell that plays an essential immunologic role by engulfing and digesting cellular debris and particulate antigens, including bacteria, in a process called phagocytosis. Macrophages develop from circulating monocytes that migrate from the blood into tissues throughout the body, especially the spleen, liver, lymph nodes, lungs, brain, and connective tissue. Macrophages also participate in the immune response by producing and responding to inflammatory cytokines.

The term "a cell line characterized by expression of monocyte/macrophage cell markers" in the context of the present specification relates to a cell line that expresses a plurality of markers selected from the group comprising CD2, CD11b, CD14, CD16, CD31, CD56, CD62L, CD64, CD68, CD115, CD163, CD192, CX3CR1, CXCR3, CXCR4. Often, these cell lines will lack lineage markers for T cells, B cells, NK cells and DC cells, such as: NK1.1, CD90, CD45R and CD11c. Examples of cell lines characterized by expression of monocyte/macrophage cell markers are the Human monocytic leukaemia cell line (thp-1) or the U937 cell line.

The term "dendritic cell" in the context of the present specification relates to a type of white blood cell that is specialized in processing antigen material and presenting it on their cell surface to the T cells of the immune system. Immature states of dendritic cells, namely dendritic progenitors, plasmacytoid dendritic cells (PDC) and pre-classical dendritic cells (pre-cDC) circulate in the blood (FIG. 13, proposed model).

The term "fibroblast" in the context of the present specification relates to a type of cell that synthesizes extracellular matrix components including glycosaminoglycans, reticular and elastic fibers, glycoproteins and collagen. Besides their important role as structural components, fibroblasts are also critical in the immune response to a tissue injury. The term "fibroblast" in the context of the present specification is meant to encompass "myofibroblasts". Myofibroblasts are positive for expression of the intermediate filament vimentin, for "alpha smooth muscle actin" (human gene=ACTA2) and for palladin, which is a cytoskeletal actin scaffold protein.

The term "low density lipoprotein (LDL)" in the context of the present specification relates to a complex particle having a highly hydrophobic core comprising polyunsaturated fatty acids, cholesterol molecules in esterified and unesterified form and varying numbers of triglycerides and other fats. The hydrophobic core is surrounded by a shell of phospholipids and unesterified cholesterol, as well as by a single copy of Apo B-100. The LDL particle also comprises approx. 80 to 100 additional ancillary proteins. For the purpose of defining the term herein, any lipoprotein fraction derived of a human blood product (particularly plasma) having the following characteristics shall be deemed to be encompassed by the term: total cholesterol content ≥4000 mg/dL (by enzymatic determination); triglyceride ratio ≤0.9 (trigylcerides/total cholesterol); electrophoresis behaviour: one major band consistent with LDL, no HDL detected.

The term "lipopolysaccharide (LPS)" in the context of the present specification relates to a large molecule consisting of a lipid and a polysaccharide composed of 0-antigen, outer core and inner core joined by a covalent bond. LPS is known to elicit a strong immune response in animals.

DETAILED DESCRIPTION OF THE INVENTION

According to a first aspect, the invention provides a method for the generation of a layered cellular three dimensional microtissue aggregate, comprising the following steps:
a. Providing a population of myeloid cells, wherein said myeloid cells are provided
   i. ex-vivo from a patient by isolation from fresh blood using a double gradient centrifugation; or
   ii. as cell culture (ex vivo) or cell line characterized by expression of monocyte/macrophage cell markers.
b. Differentiation-priming step: In this step, myeloid cells are contacted with a protein kinase C agonist, yielding primed myeloid cells. The myeloid cells are provided ex-vivo from a patient or as a cell line characterized by expression of monocyte/macrophage cell markers.
c. Culture step: In this step, the primed myeloid cells are incubated in the presence of low-density lipoprotein (LDL) in a confined volume, particularly a hanging drop culture; yielding a 3-dimensional culture, particularly a sphere, of myeloid cells.
   Subsequently, fibroblasts in medium are added to the 3-dimensional culture.
d. Co-culture step: In this step, the 3-dimensional culture of myeloid cells is incubated together with fibroblasts in a confined volume, particularly in a hanging drop culture in the presence of LDL, yielding the layered cellular 3 dimensional microtissue aggregate.

The generated layered cellular aggregate serves as a bioengineered 3D model of a human atherosclerotic plaque. The bioengineered plaque architecture is characterized by a spheroid core of monocytes. Macrophages and dendritic cells embedded in a collagenous and cholesterol rich matrix, surrounded by a thin layer of fibroblasts or myofibroblasts. The model represents the first human late-stage atherosclerosis model.

In certain embodiments, the protein kinase C agonist is a phorbol ester. In certain embodiments, the protein kinase C agonist is phorbol 12-myristate 13-acetate (PMA).

In certain embodiments, the cells provided ex-vivo from a patient by isolation from fresh blood using a double gradient centrifugation are different types of monocytes and precursors of dendritic cells circulating in the blood. Precursors of dendritic cells circulating in the blood include plasmacytoid dendritic cells and pre-classical dendritic cells.

In certain embodiments, the myeloid cells are thp-1 cells. The thp-1 cell line is commercially available and easy to expand and maintain in culture. The differentiating-priming process according to the present invention can be applied to thp-1 cells leading to successful cell differentiation and to the induction of both pro-inflammatory and remodeling genes.

Pseudo plaques generated from thp-1 cell (t plaques) and from freshly isolated monocytes or cells from human biopsies (h plaques) show similar population distribution profiles obtained from flow-cytometry analysis In certain embodiments, the myeloid cells are contacted with 5-200 ng/ml PMA in the differentiation-priming step. In certain embodiments, the myeloid cells are contacted with 5-50 ng/ml PMA in the differentiation-priming step. In certain embodiments, the myeloid cells are contacted with 10 ng/ml PMA in the differentiation-priming step. In certain embodiments, the myeloid cells are contacted with PMA for 36-120 hours in the differentiation-priming step. In certain embodiments, the myeloid cells are contacted with PMA for 48-96 hours in the differentiation-priming step. In certain embodiments, the myeloid cells are contacted with PMA for 72 hours in the differentiation-priming step.

In certain embodiments, subsequently to said differentiation-priming step and prior to said culture step, the primed myeloid cells are contacted with lipopolysaccharide (LPS).

In certain embodiments, subsequently to said differentiation-priming step and prior to said culture step, the primed myeloid cells are contacted with 10-100 ng/ml LPS for 30 min-3 hours. In certain embodiments, subsequently to said differentiation-priming step and prior to said culture step, the primed myeloid cells are contacted with 10 ng/ml LPS for 1 hour.

In certain embodiments, the myeloid cells are human myeloid cells.

In certain embodiments, the fibroblasts are human fibroblasts. In certain embodiments, the fibroblasts are myofibroblasts. In certain embodiments, the fibroblasts are human umbilical cord myofibroblasts.

By using human monocytes and human fibroblasts, the method according to the invention uses the cell types which are physiologically relevant for human atherosclerosis.

The layered cellular 3 D microtissue aggregate generated by the method according to the invention is characterized by a pathophysiological tissue environment characterized by the presence of collagen and LDL, key atherosclerotic plaque components observed in human plaques formed in vivo. In certain embodiments, collagen and LDL are present in concentrations similar to those observed in human plaques formed in vivo.

The layered cellular 3 D microtissue aggregate generated by the method according to the invention is characterized by a tissue specific cell composition similar to that observed in human plaques. This is achieved by the differentiation-priming step. The differentiation-priming step allows for the presence of both pro-inflammatory and remodeling macrophages/dendritic cells in the model. Additionally, fibroblasts are used to mimic the pathological anatomy of an atherosclerotic plaque.

According to an alternative to the first aspect of the invention and any embodiment thereof, a method for providing an ex-vivo human atherosclerotic plaque model is provided. In certain embodiments of this aspect of the invention, a model of a human fibroatheroma is provided.

According to a second aspect, the invention provides an in vitro engineered layered cellular aggregate, comprising
    an inner sphere comprising a plurality of myeloid cells, collagen, in particular collagen III, and cholesterol,
    an outer lining comprising fibroblasts.

The outer lining substantially encases said inner sphere. The cellular aggregate has a diameter of 100 µm-500 µm, and does not contain a pre-formed, cell-free scaffold.

The term "pre-formed" relates to the fact that the in vitro engineered layered cellular aggregate may comprise a scaffold which is formed from material deposited by the cells themselves. The in vitro engineered layered cellular aggregate does however not comprise a scaffold material (such as a microgel matrix) that was exogenously added to the plaque during its formation.

The in vitro engineered layered cellular aggregate according to the invention is different from currently available atherosclerotic plaque models, which comprise gel matrices or scaffolds made from biocompatible polymers.

A disadvantage of the presence of matrices or scaffolds is that these components influence the processes within the bioengineered plug in a way that does not reflect the in vivo processes. Examples for the influence of matrices or scaffolds are:
1. They support, promote and influence cell aggregation/cell-to-cell adhesion. Therefore, models comprising them are not suitable to investigate the effects of a drug that has the primary effect of disassembling the plaque. In other words: the results would be biased by the material itself.
2. They promote targeted cell differentiation. Myeloid cells differentiate according to the stimuli received (material on which they are cultured—e.g. plastic vs silicon—or biomechanical clues). Model with matrices or scaffolds are therefore not suitable to investigate the effects of a drug that aims to target cell differentiation. The results would be again biased by the material itself.
3. They introduce xenogenic material into the co-culture. Myeloid cells could respond to the presence of the biocompatible but still xenogenic polymer by activating a cascade of pathways that could potentially bias the results.
4. They require additional material, therefore higher production costs.

Available atherosclerotic plaque models can be classified as indirect models, which contain two or more cell types without direct cell-cell contact between cells of different types or as direct models, in which the multiple cell types coexist within the same volume. A The method according to the invention comprises direct co-culture of different cell types being overlaid upon one another or placed in direct contact with one another. This technique involves the three main types of cell interaction, namely signaling via cell adhesion, via cell-ECM adhesion and via soluble factors.

In certain embodiments, the cellular aggregate has a diameter of approx. 250 µm.

In certain embodiments, the inner sphere consists essentially of a plurality of myeloid cells, collagen and cholesterol.

In certain embodiments, the inner sphere comprises residual cell culture medium.

In certain embodiments, the outer lining consists essentially of fibroblasts.

The outer lining resembles the structure of the "thin cap" of atherosclerotic plaques, which is typical of late stage atherosclerosis. The in vitro engineered layered cellular aggregate according to the invention is thus a suitable model for late stage atherosclerotic plaques, in particular fibroatheroma.

In certain embodiments, the myeloid cells are human myeloid cells.

In certain embodiments, the fibroblasts are human fibroblasts.

In certain embodiments, the plurality of myeloid cells comprises monocytes, macrophages and dendritic cells.

In certain embodiments, the plurality of myeloid cells consists of monocytes, macrophages and dendritic cells.

In certain embodiments, the monocytes, macrophages and dendritic cells, are present each present at a defined ratio.

In certain embodiments, the defined ratio is
    20%-40%, particularly 26%-36%, particularly approximately 31% of monocytes;
    25%-45%, particularly 29%-39%, particularly approximately 34% of macrophages;
    15%-45%, particularly 20%-40%, particularly approximately 31% of dendritic cells.

In certain embodiments, the plurality of myeloid cells is positive for the expression of a pro-inflammatory marker selected from the group comprising CXCL10, CCR7, IL23, PTGS1 and ALOX5.

In certain embodiments, the plurality of myeloid cells is positive for the expression of a remodelling marker selected from the group comprising CCL17, CCL26, DC-SIGN, IL10, SRB1.

The expression "the plurality of myeloid cells is positive for the expression of a marker" describes the fact that within the plurality of cells, some are positive for the expression of this marker, while others may be negative. One important feature of the invention is that the bioengineered plaque comprises myeloid cells differentiated into different subtypes, namely both pro-inflammatory and remodeling myeloid cells. Therefore, some cells within the plurality of myeloid cells are positive for pro-inflammatory markers while others are positive for remodeling markers.

According to another aspect, the invention provides a plurality, in particular a manifold of 8 or 12, more particularly 96 or 384, of
  a. the layered cellular aggregates according to the second aspect of the invention or of
  b. a layered cellular aggregate generated by the method according to the first aspect of the invention.

The small size of the bioengineered plaques allows for them to be easily hosted in a well of a 96 or 384 well tissue culture plate. The bioengineered plaque can thus be integrated in a 96-well or 384-well platform and be used for drug design and screening purposes.

According to yet another aspect, the invention provides a method to assess the likelihood of a candidate compound to be effective in a treatment of atherosclerosis, comprising the steps of
  a. providing, particularly in a hanging drop culture,
    a layered cellular aggregate generated by the method according to the first aspect of the invention, or
    a layered cellular aggregate according to the second aspect of the invention, or
    a precursor of the layered cellular aggregate obtainable by a method according to the first aspect of the invention, wherein said precursor consists of the primed myeloid cells yielded by the differentiation-priming step, or the 3-dimensional culture of myeloid cells yielded by the culture step, or a co-culture of fibroblasts and the 3-dimensional culture of myeloid cells;
  b. contacting the layered cellular aggregate or the precursor with the candidate compound; and
  c. detecting a beneficial effect of said compound on the layered cellular aggregate or on the formation of said layered cellular aggregate, in particular a beneficial effect with regard to size of the layered cellular aggregate, cellular viability or cellular aggregation within the layered cellular aggregate;
  d. assigning to the candidate compound a high likelihood of being effective in a treatment of atherosclerosis if the beneficial effect is detected.

The skilled person is aware that a beneficial effect with regard to size would be a reduced size. One way to determine the size of the layered cellular aggregate is the quantification of ps-plaque area as described in the methods section.

The skilled person is aware that during early stages of plaque formation, a reduced cellular viability and reduced cellular aggregation would be considered beneficial effects, because they prevent or slow down plaque formation.

During later stages, the formation of large necrotic areas within the plaque would be considered a negative event, because it may result in plaque rupture. A beneficial effect would therefore be a reduced necrotic area present within the plaque.

The dead cells in the necrotic area release enzymes (e.g. metalloproteinases MMP) that "bite a way through" the plaque. If plaque rupture occurs, tissue factor (also called factor III, thromboplastin, or CD142) is exposed to the vessel lumen. Thereby, the coagulation cascade is activated and thrombus formation can occur.

The necrotic area can be reduced by reducing the number of the cells that over-phagocytose LDL and die in the plaque (macrophages and dendritic cells). A way to reduce their amount is to prevent their differentiation within the plaque. A way to prevent their differentiation is to reduce their over-feeding with LDL. A way to do that is to reduce availability of LDL in the blood. Identification of new compounds able to reduce the availability of LDL in the blood is one goal of this aspect of the invention.

One way to determine the size of the necrotic area is described in the methods section.

In certain embodiments, the beneficial effect is a reduced cholesterol accumulation or reduced cholesterol load in the layered cellular aggregate contacted with the candidate compound compared to a control layered cellular aggregate not contacted with the candidate compound. If, after the addition of the candidate compound to the culturing medium (in the hanging-drop) there is less (or absent) extracellular cholesterol accumulation compared to control plaques, one can conclude that the candidate compound was successful in impairing/reducing intra-plaque cholesterol accumulation. In other words, the compound was able to impair plaque development. By way of non-limiting example, extracellular cholesterol accumulation within the ps-plaque can be measured by Filippin Blue staining as described in the methods section.

In certain embodiments, the beneficial effect is a reduced, impaired or prevented aggregation of myeloid cells in the layered cellular aggregate contacted with the candidate compound compared to a control layered cellular aggregate not contacted with the candidate compound. If, after the addition of the candidate compound to the culturing medium (in the hanging-drop) cells are unable to aggregate in a plaque like structure, or plaques that were already assembled dissolve in presence of the compound, one can conclude that the compound was successful in either preventing plaque formation or promoting plaque disaggregation.

To measure aggregation/disaggregation two parameters are defined and measured with the open access software FIJI: Roundness and Solidity. A concomitant decrease in Roundness and Solidity of the pseudo-plaque upon treatment with a candidate compound indicates the occurrence of a disaggregation process.

Roundness: $4 \times \{Area/[\pi \times (Major\ axis)^2]\}$; Where "Area" and "Major axis" are measured at the circular cross-section of the ps-plaque at the grat sphere circle.

Solidity: $[Area]/[Convex\ area]$; Where "Area" and "Convex area" are measured at the circular cross-section of the ps-plaque at the grat sphere circle.

In certain embodiments, the beneficial effect is a reduced viability of myeloid cells in the layered cellular aggregate contacted with the candidate compound compared to a control layered cellular aggregate not contacted with the candidate compound.

In certain embodiments, the beneficial effect is a reduced viability of monocytes, macrophages and/or dendritic cells in the layered cellular aggregate contacted with the candidate compound compared to a control layered cellular aggregate not contacted with the candidate compound.

An assay to measure cell viability within the ps-plaque is described in the methods section.

A reduced viability of single cell types, e.g. of monocytes, macrophages and/or dendritic cells results in a changed cell composition within the ps-plaque and may also result in an overall decrease in cell viability. By way of non-limiting example, the cell composition within the ps-plaque can be determined by immunological staining (e.g. on sections of ps-plaques or followed by flow cytometry).

If, after the addition of the candidate compound to the culturing medium (in the hanging-drop) the resulting cell composition of the 3D model changes (e.g. dendritic cells are reduced compared to untreated) one can conclude that the compound has a targeted effect on a specific plaque population.

According to yet another aspect, the invention provides a method for identifying a biomarker of atherosclerosis, comprising the steps of
a. providing, particularly in a hanging drop culture, a first layered cellular aggregate generated by the method according to the first aspect of the invention, or a first layered cellular aggregate according to the second aspect of the invention, wherein the myeloid cells comprised in the first layered cellular aggregate have been provided from a patient suffering from monogenic familial hypercholesterolemia;
b. comparing the transcriptome and/or proteome of the first layered cellular aggregate with the transcriptome and/or proteome of a control layered cellular aggregate according to the invention (not comprising myeloid cells from a patient suffering from familial hypercholesterolemia, but only myeloid cells of a healthy person);
c. identifying a protein or mRNA that is upregulated or downregulated in the first layered cellular aggregate compared to the control layered cellular aggregate, thereby identifying the biomarker of atherosclerosis.

An alternative to this aspect of the invention provides a method for identifying a biomarker of atherosclerosis by comparing a first layered cellular aggregate and a control layered cellular aggregate according to the invention, wherein both layered cellular aggregates mimic different, defined plaque stages.

The bioengineered plaque allows for measuring translational biomarkers and/or can be used for basic understanding of late stage-stage atherosclerosis disease phenomena including plaque calcification and rupture. The bioengineered plaque can be integrated in other complex bioengineered dynamic systems to improve current tissue engineered vascular atherosclerosis models.

The bioengineered plaque facilitates the prediction of the main triggers of atherosclerosis, estimation of disease risk level, determination of suitable treatments and the control of the efficacy of potential treatment options.

Familial hypercholesterolemia (FH) is a genetic disorder characterized by high cholesterol levels, specifically very high levels of low-density lipoprotein (LDL) cholesterol, in the blood. FH patients have an increased atherosclerosis risk and exhibit increased atherosclerotic plaque formation. There exist several causative mutations for monogenic familial hypercholesterolemia, the most common being mutations in LDLR, ApoB or PCSK9. The bioengineered plaque according to the invention allows for the identification of mutation-dependent differences in plaque architecture, cellular composition, cell metabolism and viability within the plaque, and thus for mutation-dependent disease prognosis.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

BRIEF DESCRIPTION OF THE FIGURES

FIG. 2 shows surface expression levels of key markers in different myeloid subsets. 15 cell populations were identified using the vi-SNE workflow. Each myeloid population retains a specific surface marker expression pattern indicated by the heat-map. The present heat-map represents the median fluorescence intensity of each marker in each myeloid subset and was computed using total of 112,000 events; n=7; 2,000 randomly selected events for each sample analysed (samples analysed for both b and t plaques: Mo, pMf/d, T2, T2L).

Figure 1:
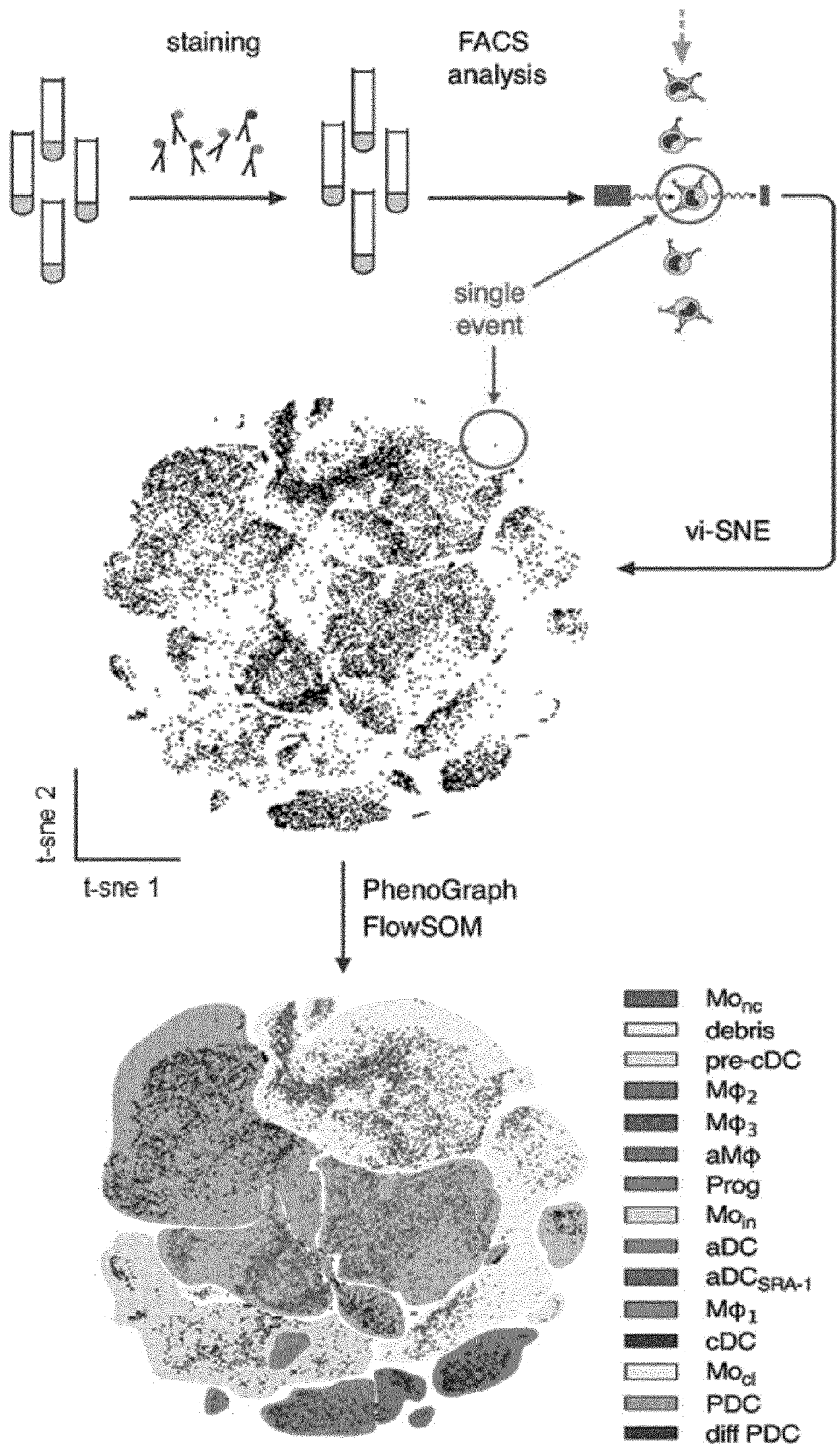
FIG. 1 shows the identification of different myeloid subsets using the vi-SNE workflow. Samples are stained and acquired at the FACS analyser. The resulting FCS files are processed to generate vi-SNE maps. Each cell recorded (single event) is positioned in a specific area of the high-dimensional space, here represented with commonly used FACS biaxial plots. Different myeloid subsets are positioned in separate regions of the high-dimensional space according to surface marker similarities. Distances between cells are representatives of cell proximity in high-dimensional rather than two-dimensional space. These myeloid subsets are automatically gated with using PhenoGraph and FlowSOM algorithms and identified in the vi-SNE map with different colours.

Table 1 shows myeloid populations in ps-plaques and native carotid plaques.

List 1 shows a primer table. Gene of interest, forward (FW) and reverse (RV) primer sequences are listed.

EXAMPLES

Example 1: Methods

Isolation of myeloid cells from blood.
Myeloid cells were isolated from fresh human blood using a double gradient centrifugation. The blood was provided by the Zurich blood bank (Blutspende Zürich—Nr.6676) and maintained at room temperature in slow rocking motion until processing. First, 20 ml of blood from each donor were diluted 1:2 with 1×PBS (Sigma) at room temperature and layered onto a Ficoll™ solution (1.077 g/ml, Sigma). Samples were then centrifuged at 400 g for 30 min without break. Second, a 46% iso-osmotic Percoll™ gradient was performed to separate the lymphocytes from the PBMCs as previously described (Menck, K., J Vis Exp, e51554, doi: 10.3791/51554 (2014)). Briefly, the buffy coat was re-suspended in 20 ml of xVivo15™ chemically defined medium (Lonza) without red phenol and carefully layered on top of a Percoll™ solution prepared with 50% RPMI medium with red phenol (Sigma), 46% Percoll™ (GE Healthcare) and 4% 1×PBS (Sigma). The second gradient was centrifuged at 550 g for 30 min without break and the white cell ring at the interphase was collected for further processing.

Myofibroblasts isolation.

Human umbilical vein myofibroblasts (HUVM) were isolated from human umbilical cords. The tissues were processed in accordance to the ethical permit released by the Kantonale Ethikkommission Zürich (KEK-Stv-21-2006). Briefly, umbilical cords were stored after labor at 4° C. in DMEM medium (Sigma) prepared with 10% FBS (Gibco), 1% GlutaMax™ (Gibco) and 1% Penn/Strep (Gibco) for maximum 2 h prior to processing. The umbilical vein was carefully extracted from the umbilical cord and the inner lumen was flashed twice with 1×PBS. The adventitia layer was peeled off with the help of forceps and scalpel. The intima layer was removed by incubating the inner lumen for 30 min in a 1 mg/ml collagenase/dispase (Roche) solution in 1×PBS. The remaining endothelial cells were washed out from the lumen with 1×PBS. The remaining media layer was minced into small pieces of approximately 2 mm length and let adhere for 10 min on the bottom of a petri dish. The tunica media fragments were then covered in DMEM medium and maintained at 37° C., 5% $CO_2$ and 95% humidity. The medium was replaced every 48 h. After about 20 days myofibroblasts sprouting from the minced pieces reached about 80% confluence and were ready for sub-culturing.

Cell culture.

HUVM were cultured in DMEM medium with 10% FBS and 1% GlutaMax™ and the medium was replaced every 48-72 h. For sub-culturing, HUVM were detached using trypsin 0.5% (Sigma) for 4 min and seeded at a cell density of 4,000 cells/cm$^2$. HUVM were expanded up to passage 5 prior to use for the experiments in this study. Human monocytic leukaemia cell line (thp-1) isolated from the peripheral blood of a 1-year-old human male with acute monocytic leukemia, were purchased from Sigma. Thp-1 cells were cultured in suspension in xVivo15™ medium and the medium was replaced every 2-3 days. Thp-1 cells were seeded at a density of about 100,000 cells/ml and sub-cultured at a density of 800,000 cells/ml.

Ps-plaque biofabrication.

The pseudo-plaque production pipeline encompasses three steps: differentiation, priming and hanging-drop. First, fresh blood-derived myeloid cells or thp-1 cells were seeded onto petri dishes for 72 h and differentiated in chemically defined xVivo15™ medium with 10% FBS in order to achieve a macrophage/dendritic cell phenotype. To induce thp-1 differentiation 10 ng/ml of phorbol 12-myristate 13-acetate (PMA, Sigma) were added to the culture medium. Second, a priming step was performed to obtain heterogeneous macrophage/dendritic cell populations with both pro-inflammatory and remodelling phenotypes. For this purpose the differentiated cells were rinsed in 1×PBS and treated for 1 h in xVivo15™ medium with 10% FCS and 10ng/ml lipopolysaccharide (LPS, Sigma). Finally, the primed cells were transferred in hanging-drop culture. Briefly, adhesive myeloid-derived cells were mechanically detached by 20 min incubation in 0.05 mM EDTA (Life Technologies) in ×PBS at 4° C. and gentle scraping. Cells were re-suspended at a cell density of 2.4×10$^6$ cells/ml in presence of LDL 50 µg/ml (LEE Biosolutions) in xVivo15™ medium with 10% FBS. Droplets of 10 µl were pipetted on the lead of a 10 cm diameter petri dish and kept in hanging-drop culture for 48 h. To the core of myeloid-derived cells assembled during the 48h incubation, an external layer of HUVM was added. HUVM were prepared at a cell density of 4×10$^5$ cells/ml in DMEM medium with or without 50 µg/ml LDL and 10 µl of the cell suspension were carefully added to each pre-existing drop and cultured in hanging-drop for further 48h.

Flow cytometry.

Biopsies of carotid branches were obtained from patients undergoing carotid endarterectomy and shunting, secondary to vascular stenosis (Ethik Kommission der Universität Witten/Herdecke—Nr.79/2012). Carotid plaques and bio-fabricated ps-plaques were digested with 1 mg/ml collage-nase/dispase solution in 1×PBS for 15 min at 37° C. Cells were gently pipetted through a cell strainer with the mesh size of 40 µm (Falcon) and incubated for 5 min at 4° C. with magnetic beads coated with anti CD45 antibodies, according to the provider instructions (MACS Miltenyi Biotec). CD45+ cells were magnetically sorted and stained with Zombie Aqua™ fixable viability kit (BioLegend) for 5 min and fixed over night at 4° C. in a 1% Paraformaldehyde (PFA, Sigma) solution in 1×PBS. The single cell suspension was stained for 15 min at room temperature in FACS buffer prepared with 5% FCS and 0.01% $NaN_3$ (Sigma) in 1×PBS with an optimized FACS antibody panel including: CD14-PerCP (#325631, Biolegend), CD16-Alexa700 (#360717, Biolegend), CD11b-Alexa594 (#101254, Bioegend), CD11c-PE-Cy5 (#301609, Biolegend), CD36-BV605 (#563518, Becton Dickinson) and SRA-1-PE (#REA460, MACS Miltenyi Biotec). Each antibody was previously titrated to establish the optimal working concentration. Samples were acquired using LSRFortessa™ analyser (Becton Dickinson) and signal compensation was performed using OneComp eBeads™ (eBioscience).

VI-SNE Workflow.

The FCS files obtained from the FACS analysis were pre-processed using the software Flowjo (FlowJo, LLC). First, cell populations of interest were gated according to forward and side scatter (FSC and SSC) parameters. Second, singlets were gated and Zombie Aqua™ dye negative events, representing the alive population of interest, were exported for further processing. Data post-processing was performed using the R platform and the Cytofkit package. Briefly, pre-processed FCS files from each sample were loaded onto Cytofkit, randomly down-sampled to 2,000 events (ceil; n=2,000) and computed using t-Distributed Stochastic Neighbor Embedding (t-SNE) algorithm (Van Der Maaten, L, J Mach Learn Res 9, 26 (2008)). Each event recorded was positioned in a specific location of the high-dimensional space. The output was a vi-SNE biaxial plot where distances between events are representatives of cell proximity in high-dimensional rather than two-dimensional space. The proximity between events is based on similarities in surface marker expression levels. Different myeloid subsets were positioned in separate regions in high-dimensional space according to surface marker similarities. Automatic gating of myeloid subsets was performed through a preliminary clustering step with PhenoGraph algorithm (k=42) and a following metaclustering step with FlowSOM algorithm (k=10).

Immunofluorescence and Immunohistochemistry.

Myofibroblasts were fixed for 20 min in 4% PFA in 1×PBS and maintained in 1×PBS at 4° C. until further processing and not more than 7 days. Cells were stained with the primary antibodies anti-alpha smooth muscle actin (aSMA, # ab7817, Abcam) and anti-smooth muscle myosin heavy chain (SMMHC, # ab53219, Abcam) overnight at 4° C. and with secondary antibodies (anti-mouse #715-605-151, Jackson Immuno Research; anti-rabbit # A11008, Life Technologies) and phalloidin (# A12381, Life technologies) for 1 h at 37° C. Nuclei were counterstained with DAPI and the slides were mounted in Vectaschield® (Vector Laboratories). The ps-plaques were carefully washed in 1×PBS and fixed in PFA as described above. Plaques were dehydrated overnight in a solution of 25% sucrose (Sigma) in 1×PBS, embedded in OCT matrix (CellPath) and stored at −20° C. Slices of 5 μm were cut, rehydrated in 1×PBS for 15 min and stained with primary antibodies: anti-Collagen type Ill (# ab7778, Abcam), anti-aSMA and anti-CD45-PeCy5 (#304009, BioLegend) overnight at 4° C. Secondary antibody staining was performed (anti-mouse, 715-545-151, Jackson Immuno Research; anti-rabbit # A11008, Life Technologies) for 1 h at 37° C. For the Filippin sections were quenched for 10 min with 1.5 mg/ml glycine (Sigma) in 1×PBS prior to addition of 250 μg/ml Filippin III dye (Sigma) at room temperature for 2 h. Sections were washed 3 times in 1×PBS and nuclei were counterstained with propidium iodide 1 mg/ml (BioLegend) for 5 min. Slides were mounted in Vectaschield®. Images were acquired in grey scale with the confocal microscope (Leica SP8). Image post-processing, specifically the choice of appropriate pseudo-colours, was performed using ImageJ.

RT-qPCR.

Total RNA was extracted using the GenElute Mammalian Total RNA Kit (Sigma), following the manufacturer's instructions. Reverse transcription was performed for each sample in a 20 μl reaction mixture containing 1 μg of RNA, 1×PCR buffer, 5 mM $MgCl_2$, 10 mM of each dNTP, 0.625 μM oligo $d(T)_{16}$, 1.875 μM random hexamers, 20 U RNase inhibitor and 50 U MuLV reverse transcriptase (all from Life Technologies). The conditions for the reverse transcription were the following: 25° C. for 10 min, 42° C. for 1 h, followed by 99° C. for 5 min. The resulting cDNA was amplified in duplicate by quantitative real-time PCR in 10 μl reaction mixture with 200 nM of each specific primer (List 1) and 1×Fast Syber Green qPCR MasterMix (Applied Biosystems). For the amplification reaction, StudioQuant 7 was used (Applied Biosystem). The amplification program was set as follows: 95° C. for 5 min, followed by 40 cycles at 95° C. for 10 sec, 60° C. for 15 sec, 72° C. for 20 sec. GAPDH and 18S served as housekeeping genes and their amplification data were averaged and used for sample normalization. The software Excel (Microsoft) was used for the comparative quantification analysis.

Ps-Plaque Viability Assay.

Cell viability within the plaque was measured using CellTiter-Glo® 3D Cell Viability Assay (Promega). Briefly, the biofabricated plaques were washed in 1×PBS and dispensed in a opaque-walled 96 well plate (Costar). Each ps-plaque (1 plaque/well) was dispensed in 15 μl of 1×PBS. Equal volume of CellTiter-Glo® 3D Reagent was added to each well for a final volume of 30 μl. Luminescence was measured after a 30 min of incubation at room temperature with SPECTRAmax® Gemini-XS (Bucher biotech) and ATP levels were reported in relative luminescence units (RLU).

Quantification of Ps-Plaque Area and Necrotic Area.

For the measure of the plaque necrotic area, every plaque was stained for 40 min in a solution of calcein (5 μM) and eth-1 (15 μM) from the LIVE/DEAD™ Viability/Cytotoxicity Kit, for mammalian cells (Life Technologies). Ps-plaques were imaged using an inverted microscope (Leica, DM IL LED) and post-processed in ImageJ. Briefly, images underwent colour 2D Parallel iterative deconvolution using the WPL method (Max number of iteration=5; Max number of threads$^2$=4). The results of the point of spread function obtained from the deconvolution were normalized and the green and red channels were thresholded with the MaxEntropy setting. The ps-plaque necrotic area was measured as necrotic area over alive area and indicated as percentage. Plaque dimension was measured using the bright field images of the plaque circular cross section. First, the image was converted to 8-bit format and thresholded with the MaxEntropy method. Second, the area of the particles was analysed from objects with a dimension larger than 1,000 px in order to exclude debris or single cells not belonging to the bioengineered plaque. Plaque area was reported in $mm^2$.

Statistical Analysis.

vi-SNE cluster counts and PCR comparative quantitations were analysed using multiple comparison analysis. First, Gaussian distribution of the data was confirmed with Shapiro-Wilk normality test. Second, repeated measures (RM) two-way ANOVA with Tukey's multiple comparison test was applied. Luminescence, plaque and necrotic area were analysed with paired t-test. All statistical analyses were performed with GraphPad Prism Version 6, GraphPad Software, San Diego, Calif., USA). Significance was accepted at $p<0.05$. All data are presented as mean±s.d.

Figure 3:
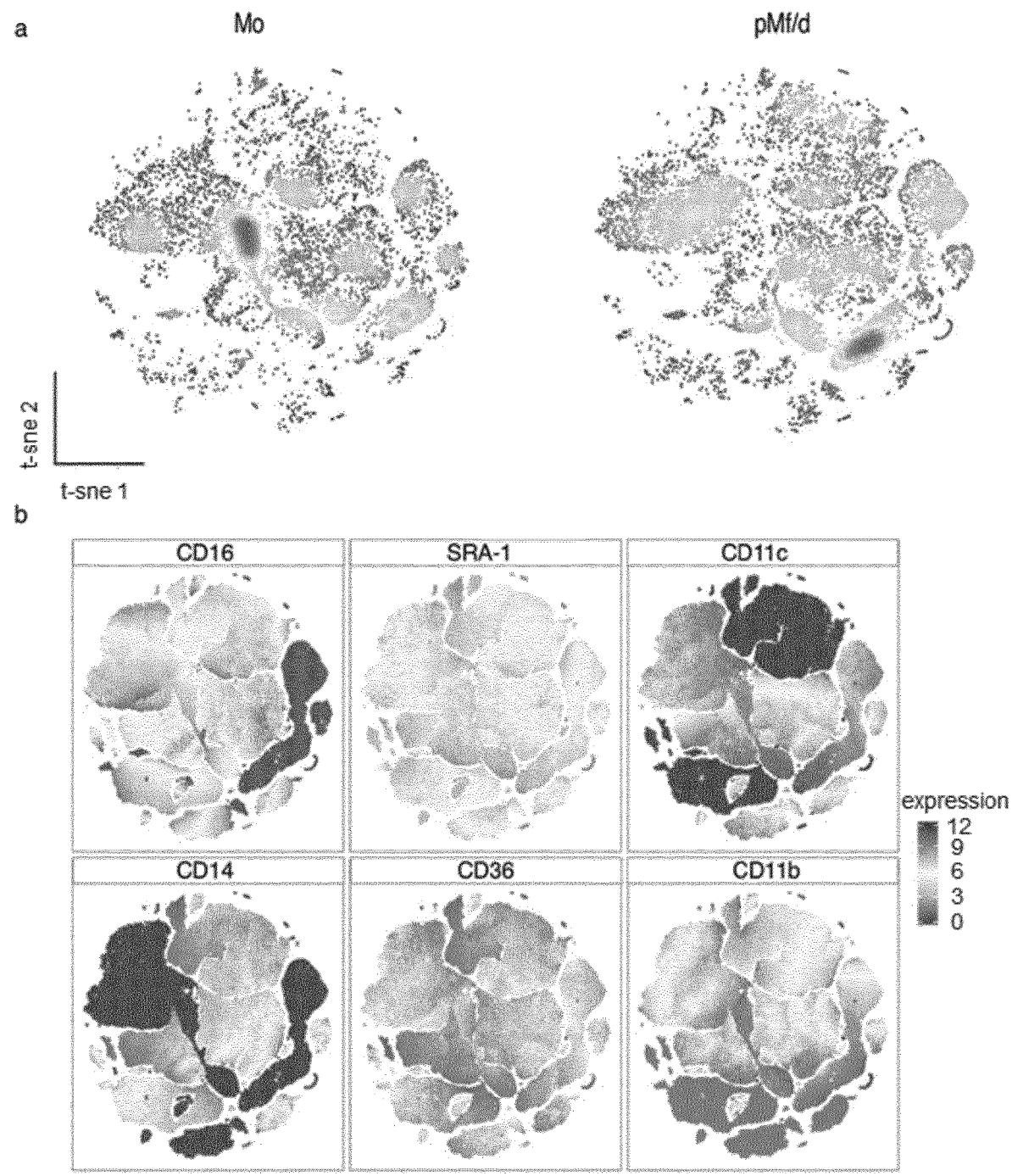
FIG. 3 shows density plots from blood-derived cells before and after differentiation-priming process. (a) Density distribution of recorded events before (Mo) and after (pMf/d) the differentiation-priming process. Areas of high event density are depicted in red and areas with low event density in blue. n=7; 2,000 randomly selected events for each sample analysed are shown (Mo and pMf/d). Therefore, in each vi-SNE maps 14,000 events are plotted. (b) Expression level plots. Each vi-SNE map shows 112,000 events; n=7; 2,000 randomly selected events for each sample analysed (samples analysed for both b and t plaques: Mo, pMf/d, T2, T2L).
Figure 4:
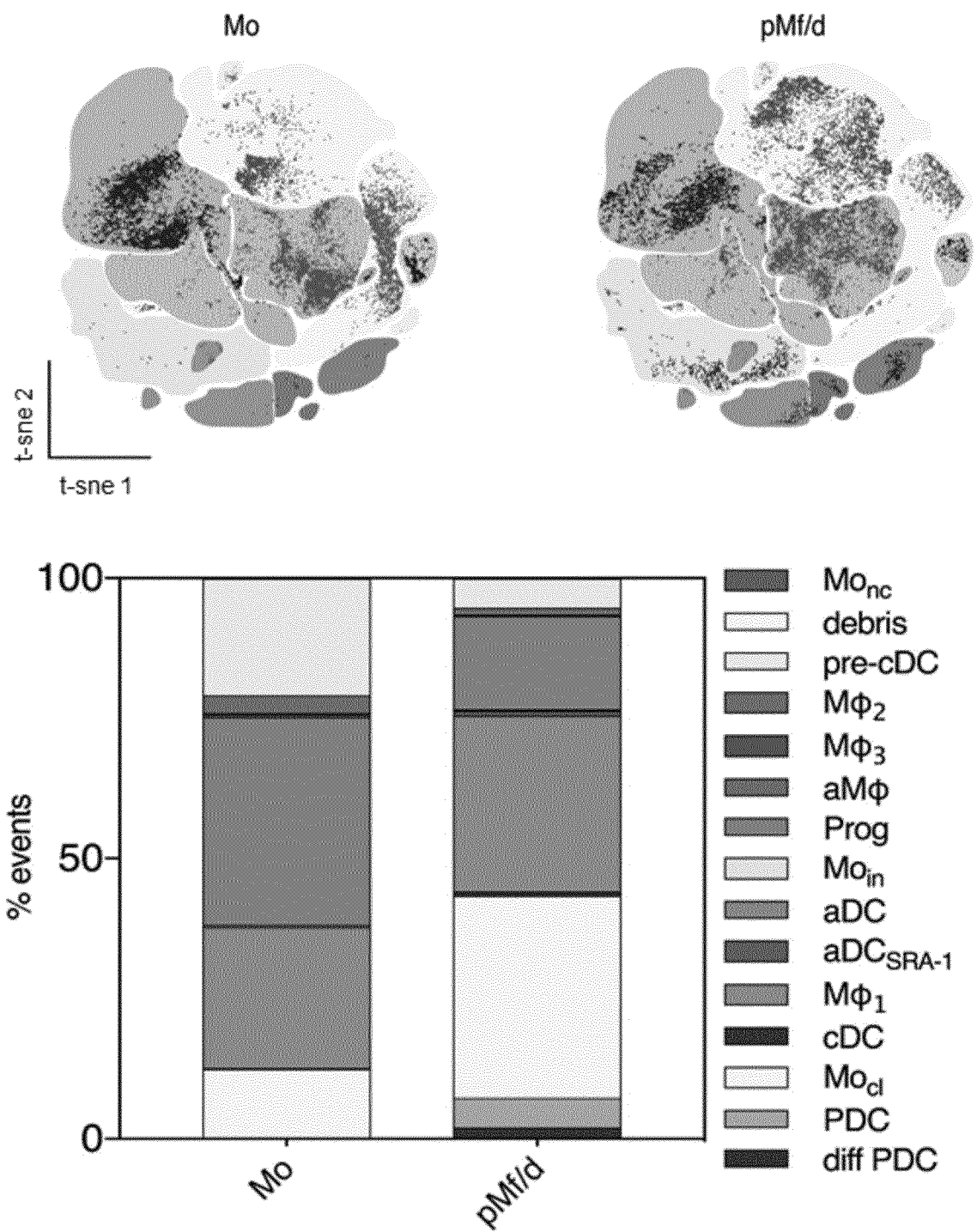
FIG. 4 shows differentiation-priming effects on thp-1 cells. vi-SNE maps indicate different myeloid populations identified within thp-1 cells at the beginning (Mo) and at the end (pMf/d) of the differentiation-priming process. The part-of-whole graph shows the % of events and summarizes the vi-SNE results. n=7; 2,000 events per sample are reported. A total of 14,000 events are shown in each vi-SNE map.
Figure 5:
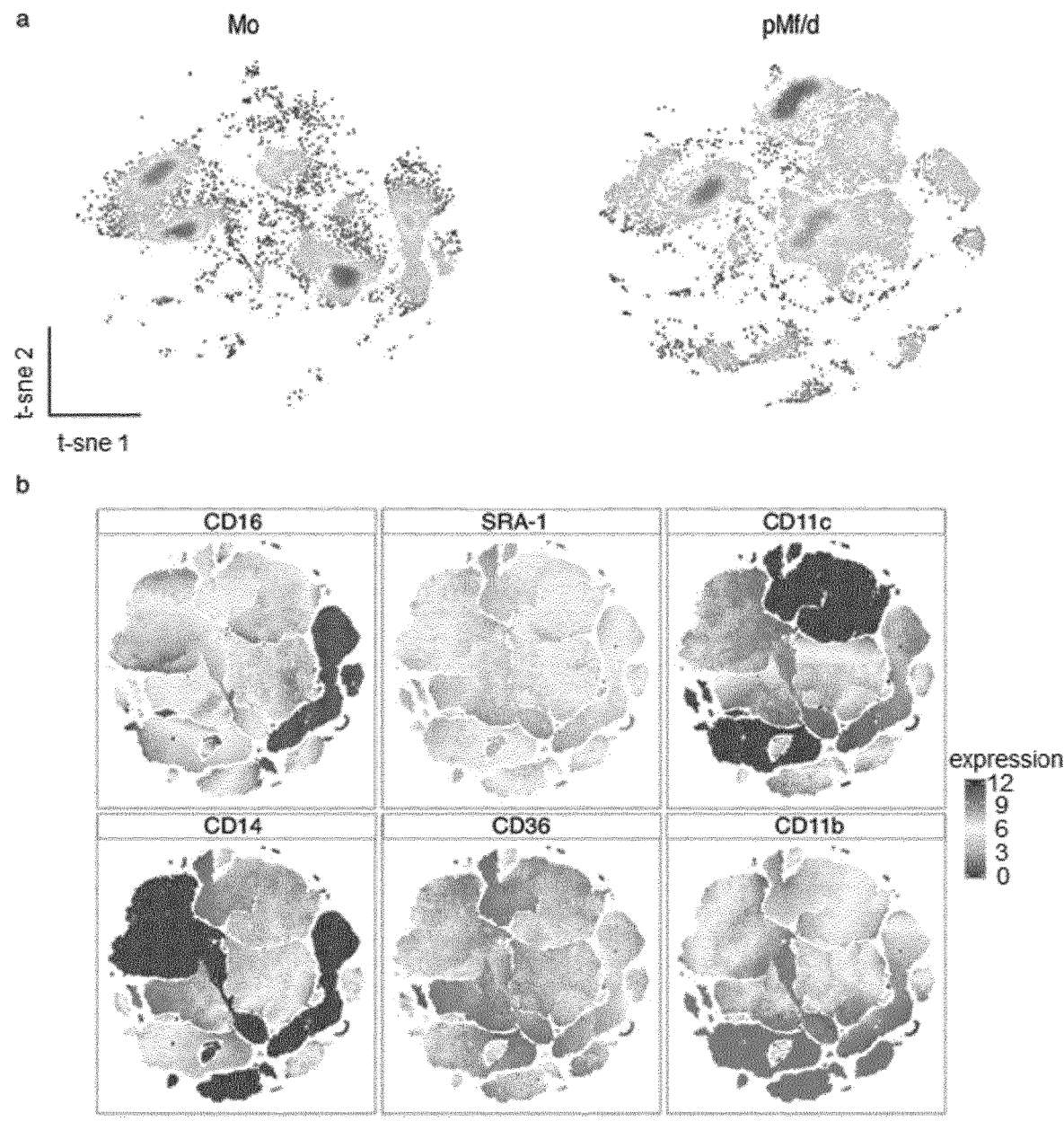
FIG. 5 shows density plots from thp-1 cells before and after differentiation-priming process. (a) Density distribution of recorded events before (Mo) and after (pMf/d) the differentiation-priming process. Areas of high event density are depicted in red and areas with low event density in blue. In each vi-SNE maps 14,000 events are plotted. n=7; 2,000 randomly selected events for each sample analysed are shown (Mo and pMf/d). (b) Marker expression level plots.
Figure 6:
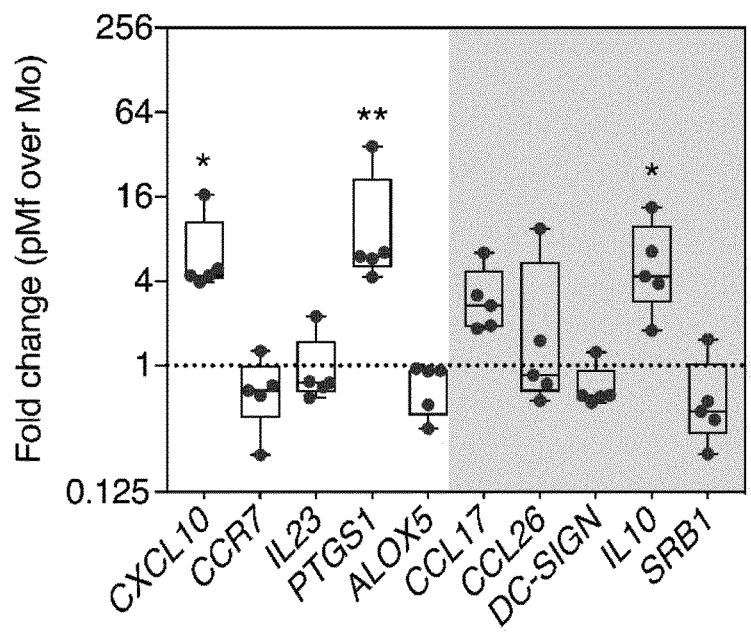
FIG. 6 shows changes in gene expression profile of thp-1 cells upon differentiation—priming. The expression profile of pro-inflammatory (left—white panel) and remodelling (right—orange panel) genes is reported in fold change over Mo expression levels (where fold change=1). Data (n=5) were normalized on the averaged GAPDH and 18S expression.
Figure 14:
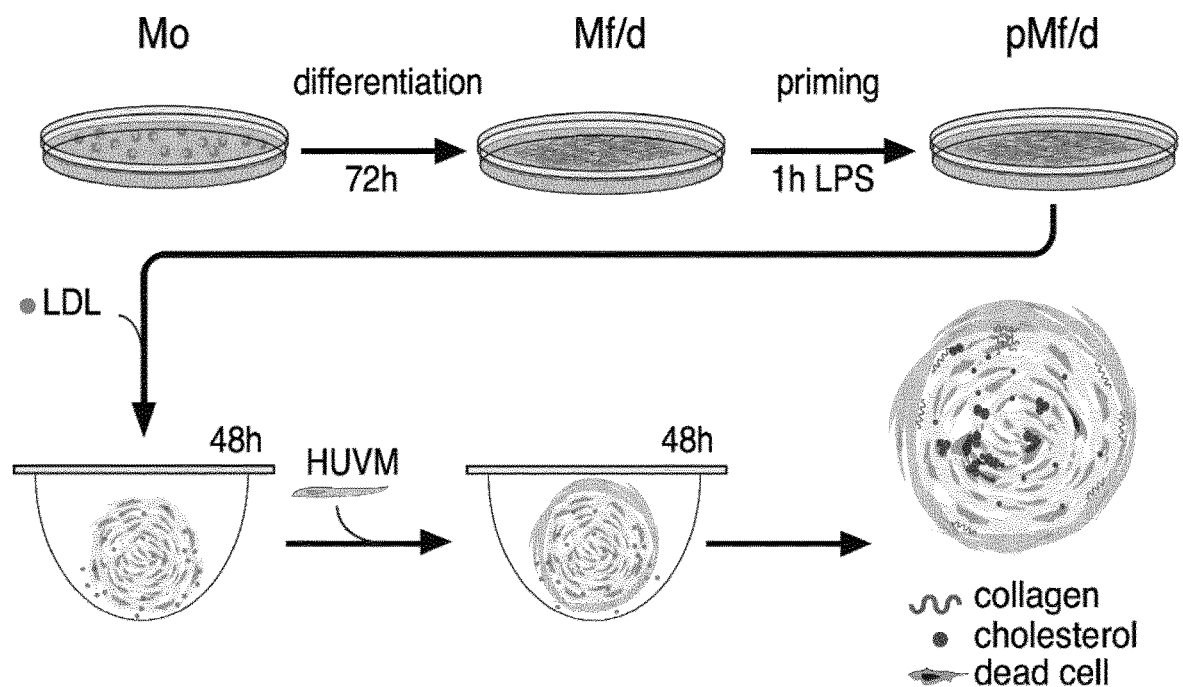
FIG. 14 shows a schematic view of the pseudo-plaque assembly including a step of cell conditioning and a step of hanging drop culture.
Figure 20:
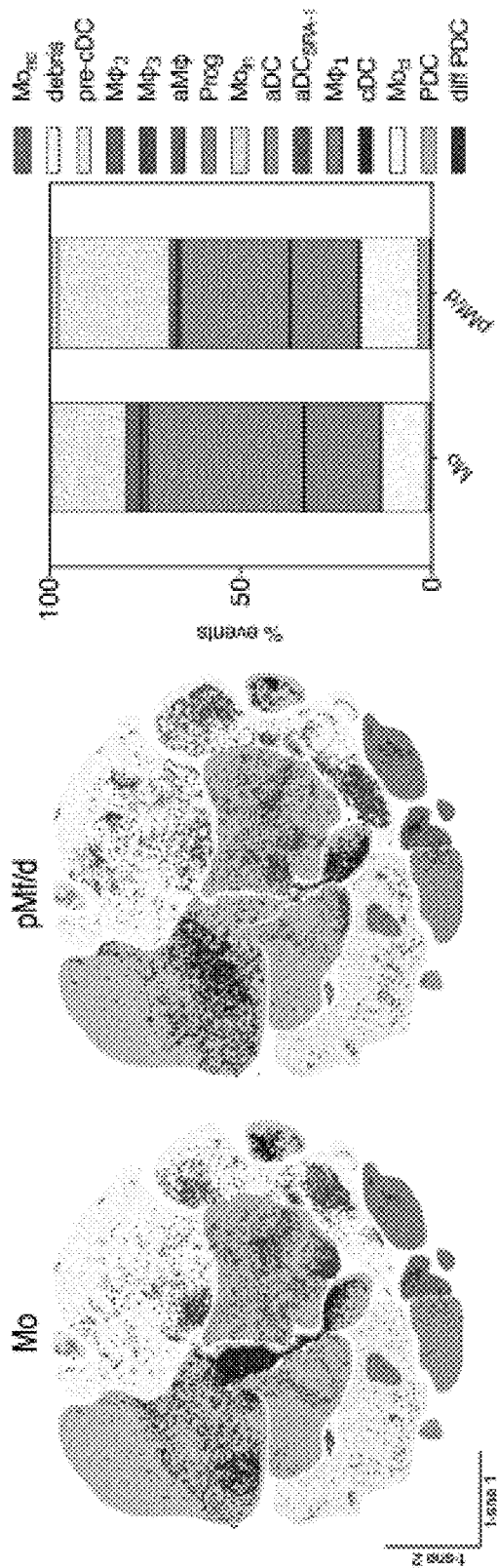
FIG. 20 shows biofabricated human atherosclerotic plaque. vi-SNE maps indicating the cell populations at the beginning (Mo) and at the end (pMf/d) of the differentiation-priming process.

Example 2: Differentiation-Priming Strategy Promotes Population Redistribution in Cells from Myeloid Origin A two-step bioengineering method for the assembly of the ps-plaque was established (FIG. 14). Myeloid cells isolated from freshly drawn blood and thp-1 cells were differentiated towards macrophage/dendritic phenotype and primed with LPS to obtain a mixed population of pro-inflammatory and remodelling cell populations. The success of the differentiation-priming strategy was verified using a fluorescence-activated cell sorting (FACS) and the results were computed using dimensionality reduction and clustering algorithms, PhenoGraph and FlowSOM respectively (Amir el, A. D., Nat Biotechnol 31, 545-552, doi:10.1038/nbt.2594 (2013)). With this technique the inventors identified 15 cell populations in the multidimensional space that they classified according to the differential expression levels of key surface markers (FIG. 20; FIG. 1; FIG. 2 and Table 1). In samples isolated from the blood the inventors identified 4 over-represented populations: classical monocytes (Mod), macrophages (WM, pre-classical dendritic cells (pre-cDC) and an unknown myeloid progenitor population (Prog) (FIG. 20; FIG. 2). Each population at the end of the differentiation-priming process was monitored and a significant decrease in the unknown myeloid progenitors (p=0.005) observed, coupled with a significant increase in pre-cDC (p=0.05) (FIG. 20). Additionally, the inventors observed a priming-induced increase in CD11c surface levels within the pre-cDC population and in the myeloid progenitors (FIG. 3). In cell samples from untreated thp-1, the inventors observed an initial population distribution similar to the one found in blood samples. When they applied the priming process to thp-1 monocytes, the inventors observed a significant reduction in the myeloid progenitors count (p<0.001). The latter was concomitant with a decrease in pre-cDC count (p<0.001) and the appearance of plasmacytoid dendritic cells (PDC) (FIG. 4, FIG. 5). Furthermore, the inventors observed that the priming process triggered the proliferation of classical monocytes (p<0.001) (FIG. 4). The inventors then analysed the expression levels of pro-inflammatory and remodelling gene targets. In blood derived cells they observed induction of CXCL10 (p<0.001), CCL17 (p<0.05), DC-SIGN (p<0.001) and SRB1 (p<0.001) upon treatment, indicating the overall stronger induction of remodelling over pro-inflammatory genes (FIG. 6). When they analysed the changes in thp-1 cells gene expression levels upon differentiation-priming, the inventors observed induction of CXCL10 (p=0.03), PTGS1 (p=0.05) and IL10 (p=0.01), indicating pro-inflammatory gene up-regulation over remodelling genes (FIG. 6).

Figure 7:
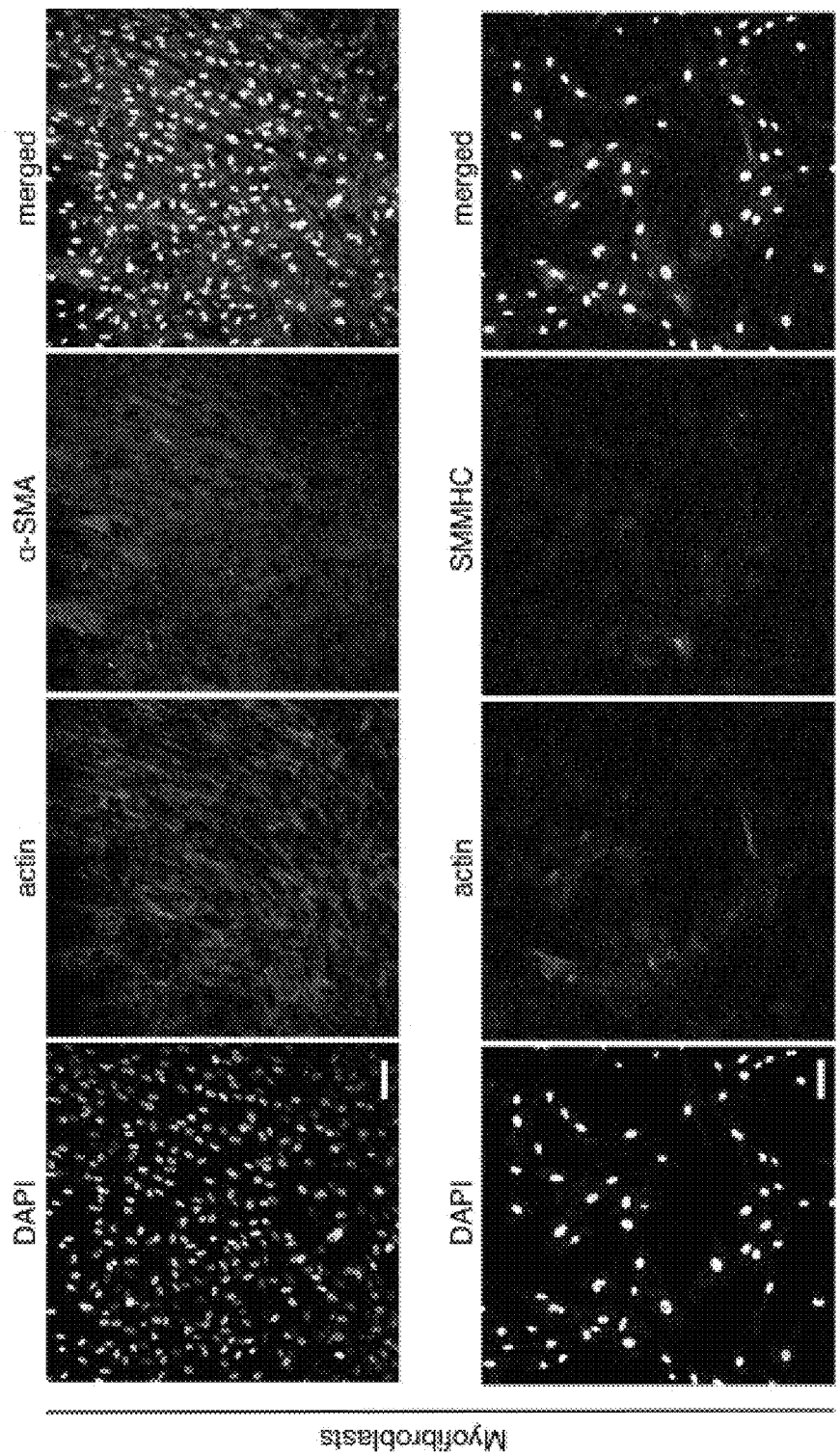
FIG. 7 shows the myofibroblasts characterization. Myofibroblasts isolated from human umbilical vein express α-smooth muscle actin (α-SMA) and smooth muscle myosin heavy chain (SMMHC); scale bar 100 µm.
Figure 15A:
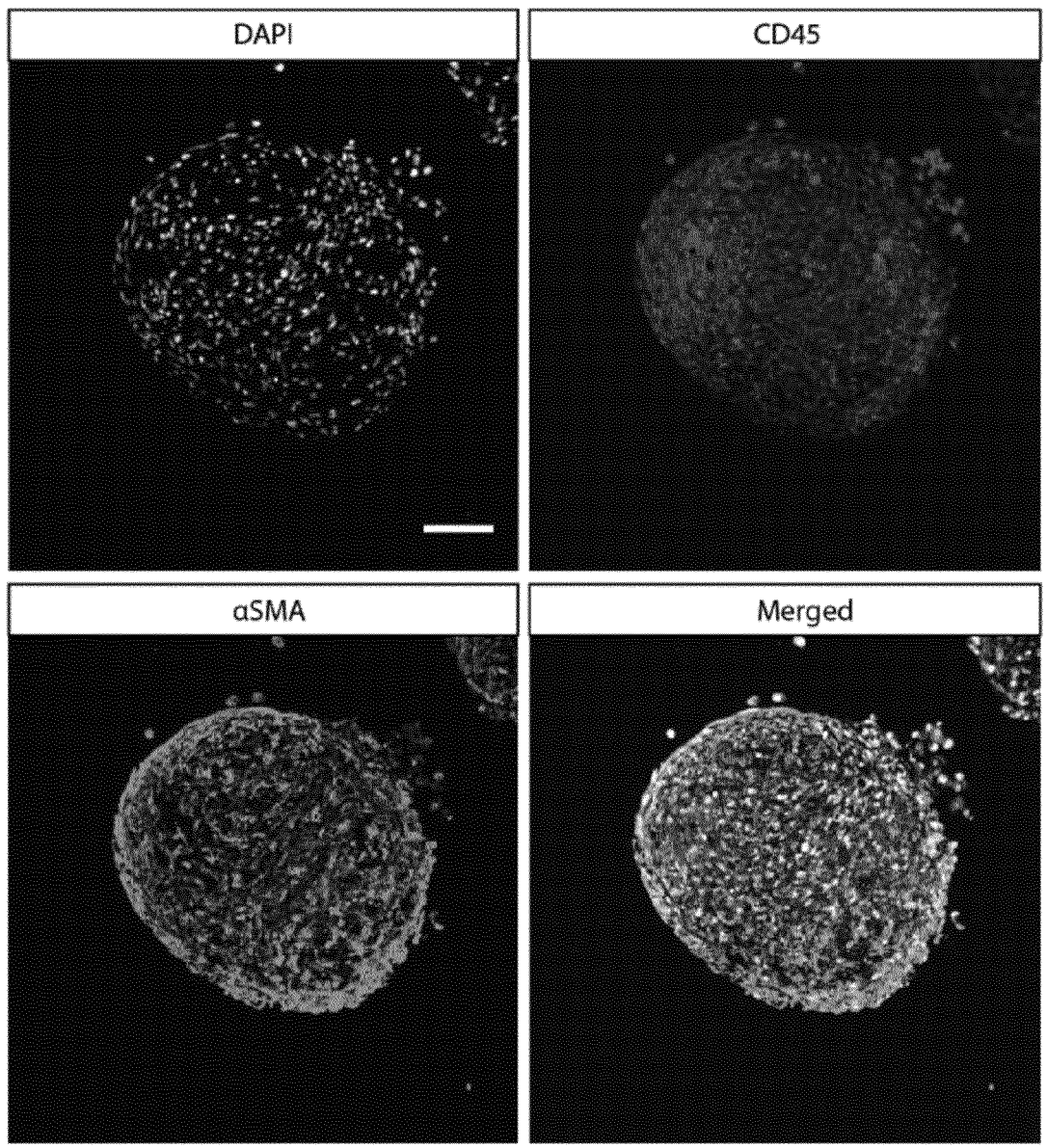
FIG. 15 shows confocal imaging of the atherosclerotic plaque. A) CD45* myeloid cells are embedded and surrounded by aSMA* fibroblasts (scale bar 100 μm). B) Collagen deposition within the bioengineered plaque (scale bar 50 μm). C) Intracellular cholesterol accumulation (scale bar 50 μm).
Figure 15B:
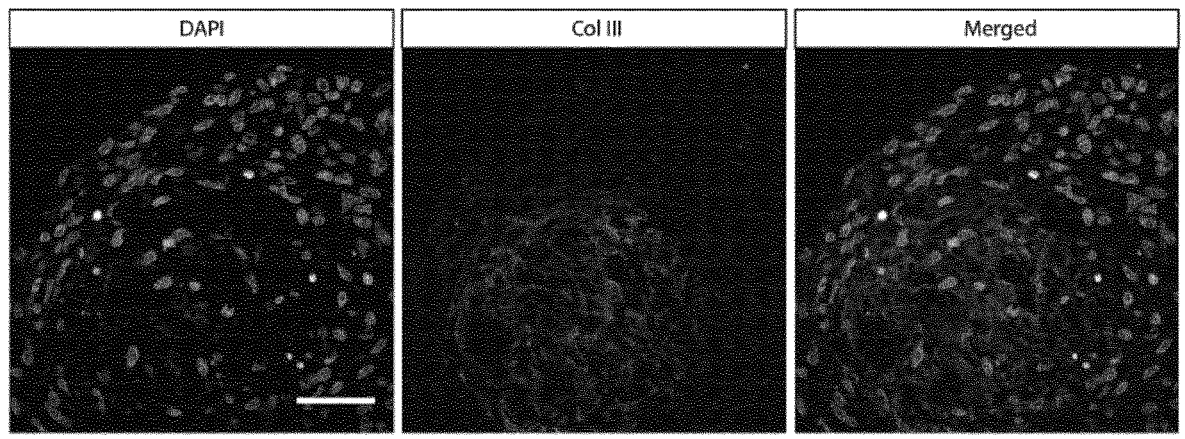
Figure 15C:
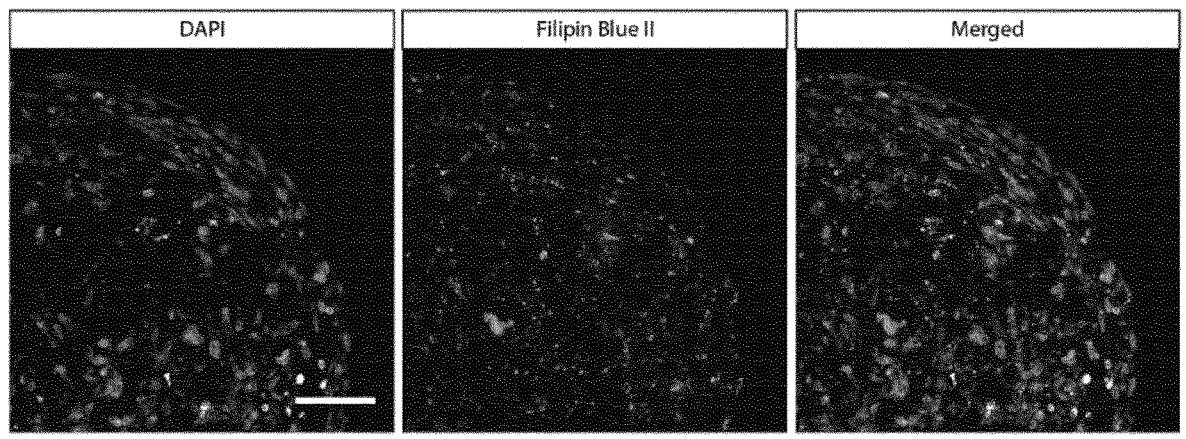

Example 3: Defining the Gravity-Guided Biofabrication of Human Atherosclerotic Plaques Primed cells were detached from the petri dish and cultured in hanging drop for 48 h to foster cell aggregation. LDL was added to the culture medium to mimic the atherosclerotic niche composition. At the end of the 48 h incubation, myofibroblasts isolated from the human umbilical vein (HUVM) were added to the hanging drop to establish a co-culture system (FIG. 14; FIG. 7). After additional 48 h the inventors observed the α-SMA+ HUVM cells integrating within the pre-existing myeloid CD45+ cell aggregates. Moreover, they observed the formation of a thin fibrotic layer around the bioengineered spheroid (FIG. 1$d$), the assembly of collagen clumps within the ps-plaque and intra-plaque accumulation of lipid aggregates (FIG. 15$b$).

Figure 8:
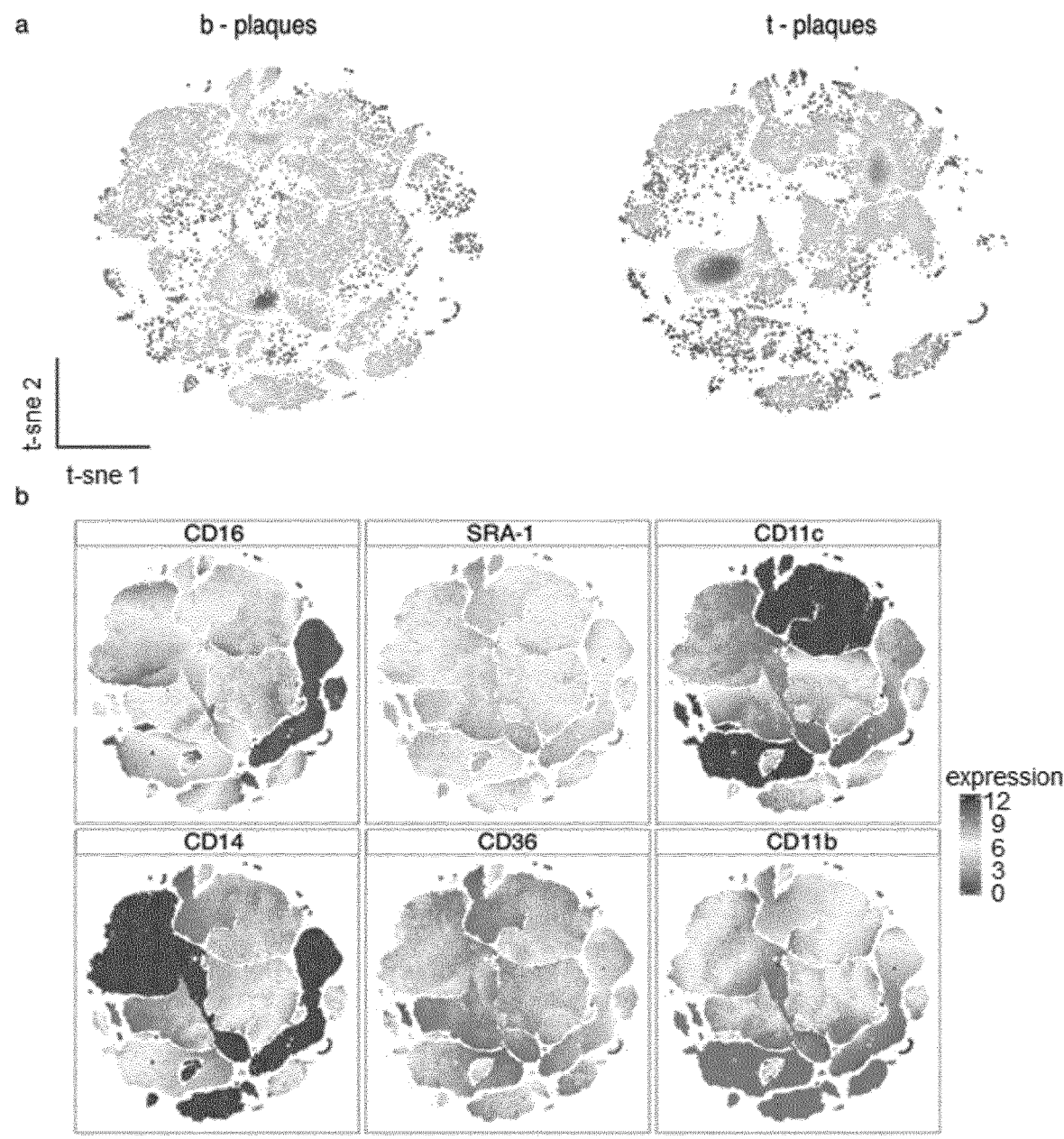
FIG. 8 shows vi-SNE comparison between bioengineered b-plaques and t-plaques. (a) vi-SNE density plots. Areas of high event density are depicted in red and areas with low event density in blue. n=7; 2,000 events per sample were randomly down-sampled from each sample. A total of 14,000 events is shown in each vi-SNE map. (b) Marker expression level plots.
Figures 9A, 9B:
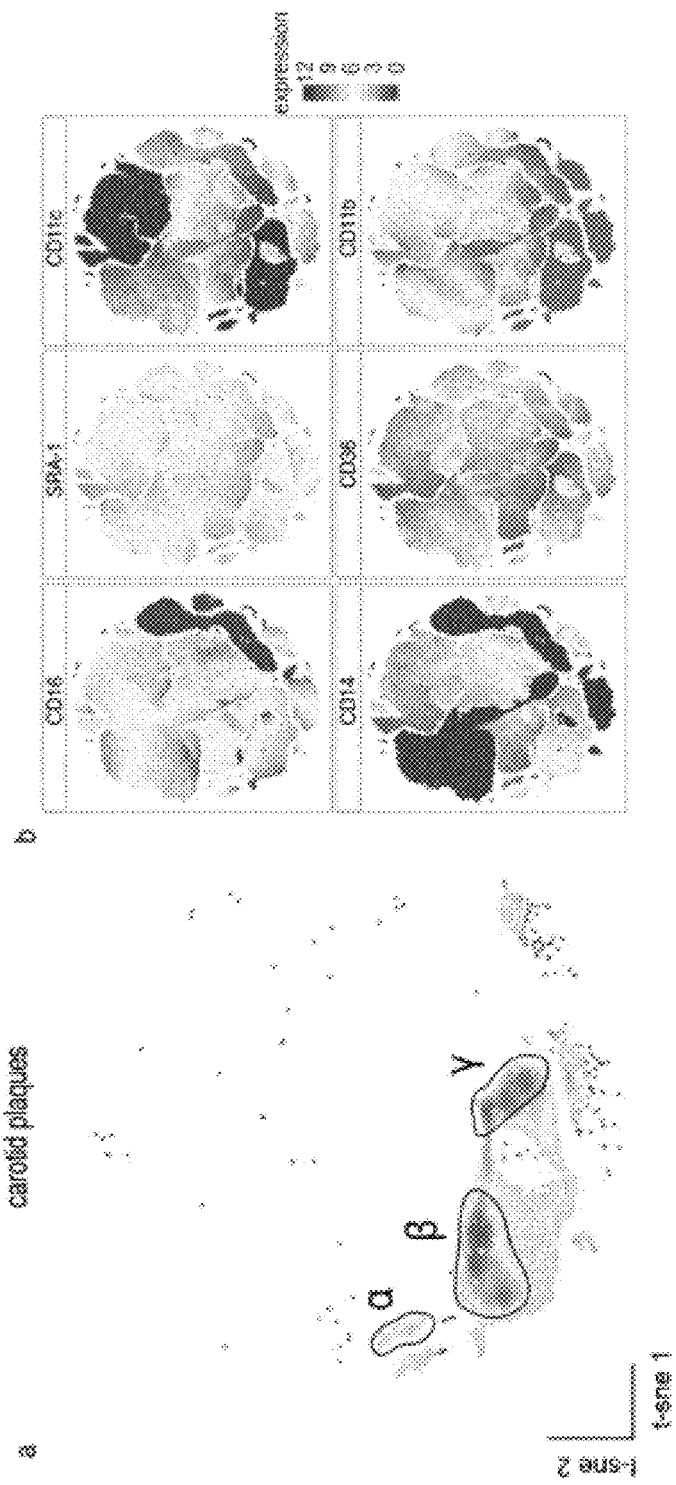
FIG. 9 shows density plots from myeloid populations isolated from native carotid plaques. (a) vi-SNE maps indicate the event density recorded in each myeloid population. Areas of high event density are depicted in red and areas with low event density in blue. PDC sub-populations are indicated in the vi-SNE map: type-α, type-β and type-γ. n=5. 2,000 events per samples are plotted for a total of 10,000 events. (b) Marker expression level plots.
Figure 16:
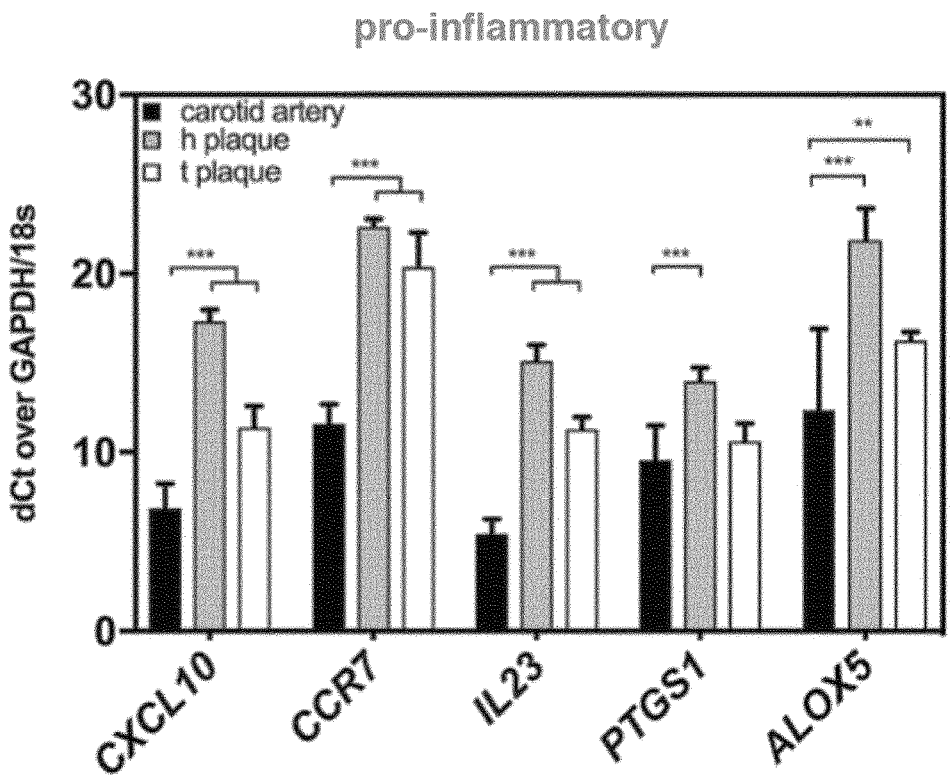
FIG. 16 shows bioengineered plaques and human carotid plaques compared with qPCR. Pro-inflammatory and remodeling gene induction levels are measured and compared in the graph; p-value: *p=0.333; *19=0.002; ***p<0.001; test: RM two-way ANOVA with Sidak correction h plaque, t plaque, carotid artery n=5.
Figure 16:
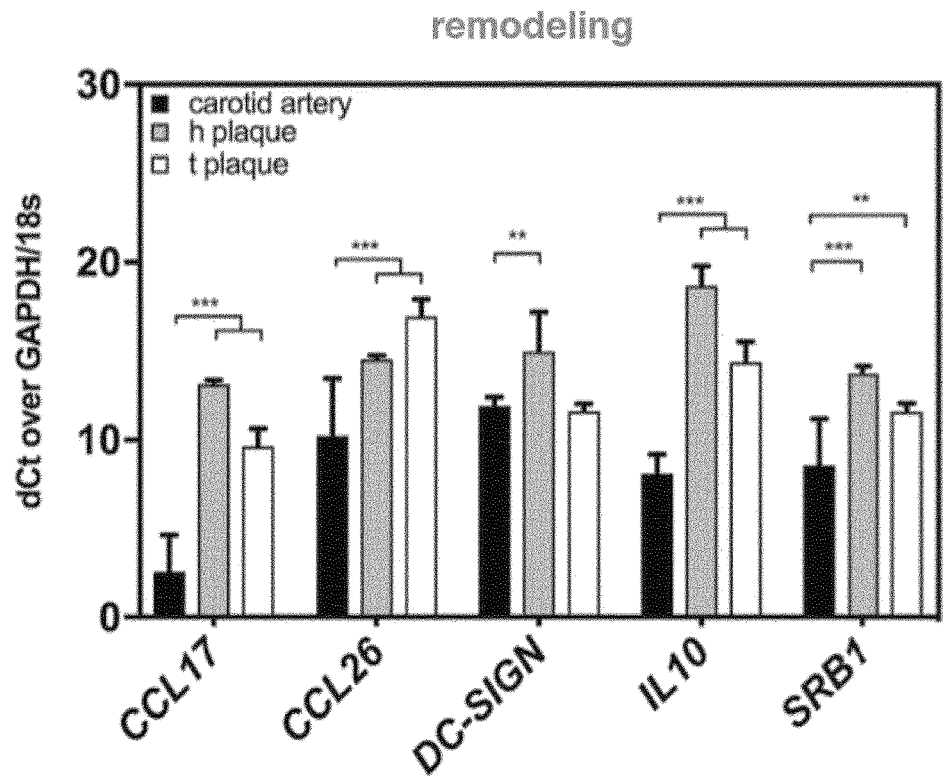
Figure 17:
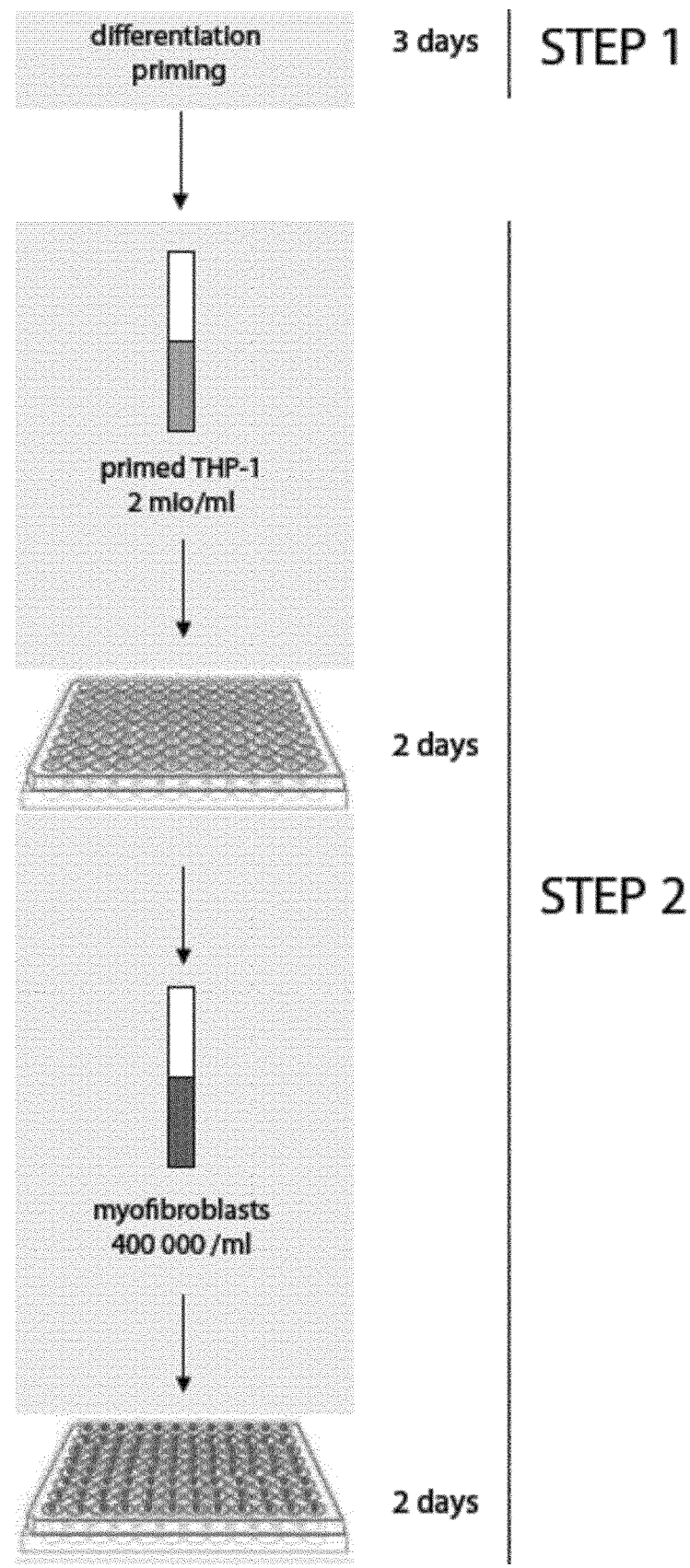
FIG. 17 shows the product production pipeline. Thp1 monocytes are cultured in vitro up to the desired concentration (about 2 mio cells for one 96 well plate). The STEP1 (differentiation-priming) lasts about 3 days (72 h+1 h). At this point the cells are detached and inserted in a robotic system for STEP2. Hanging drops of 10 μl are generated automatically on the lid of a 96 or 384 well plate. The bottom of the 96/384 well plate is automatically filled with 100 μl 1x PBS to create a humid environment necessary to keep the drop volume constant. The plates are kept at 37° C. and 5% $CO_2$ for 48 h. At this point myofibroblasts are automatically added to the forming bioengineered spheroids and the plates are be kept at 37° C. and 5% $CO_2$ for additional 48 h after one week of processing, the product is ready to be delivered to the customer.
Figures 18A, 18B, 18C, 18D:
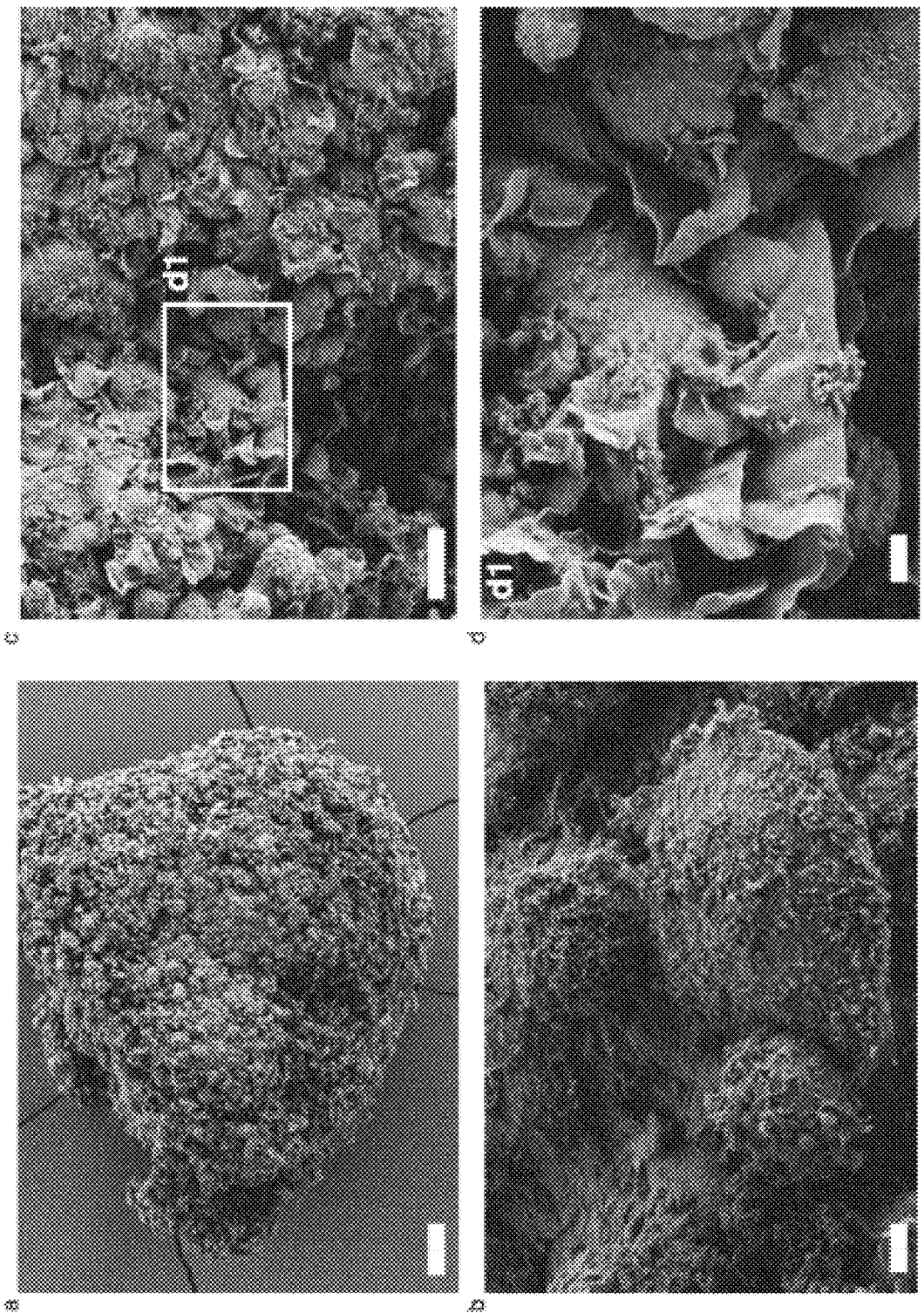
FIG. 18 shows scanning electron microscopy imaging of the ps-plaque. (a) SEM image of a ps-plaque. Scale bar 40 μm. (b) Detail of the ps-plaque external surface (myofibroblast layer). Scale bar 4 μm. (c) Inner architecture of the ps-plaque. Scale bar 4 μm. With a detail (d, d1) showing macrophage/dendritic cells surfaces in contact with LDL cholesterol. Scale bar 10 μm.
Figures 19A, 19B:
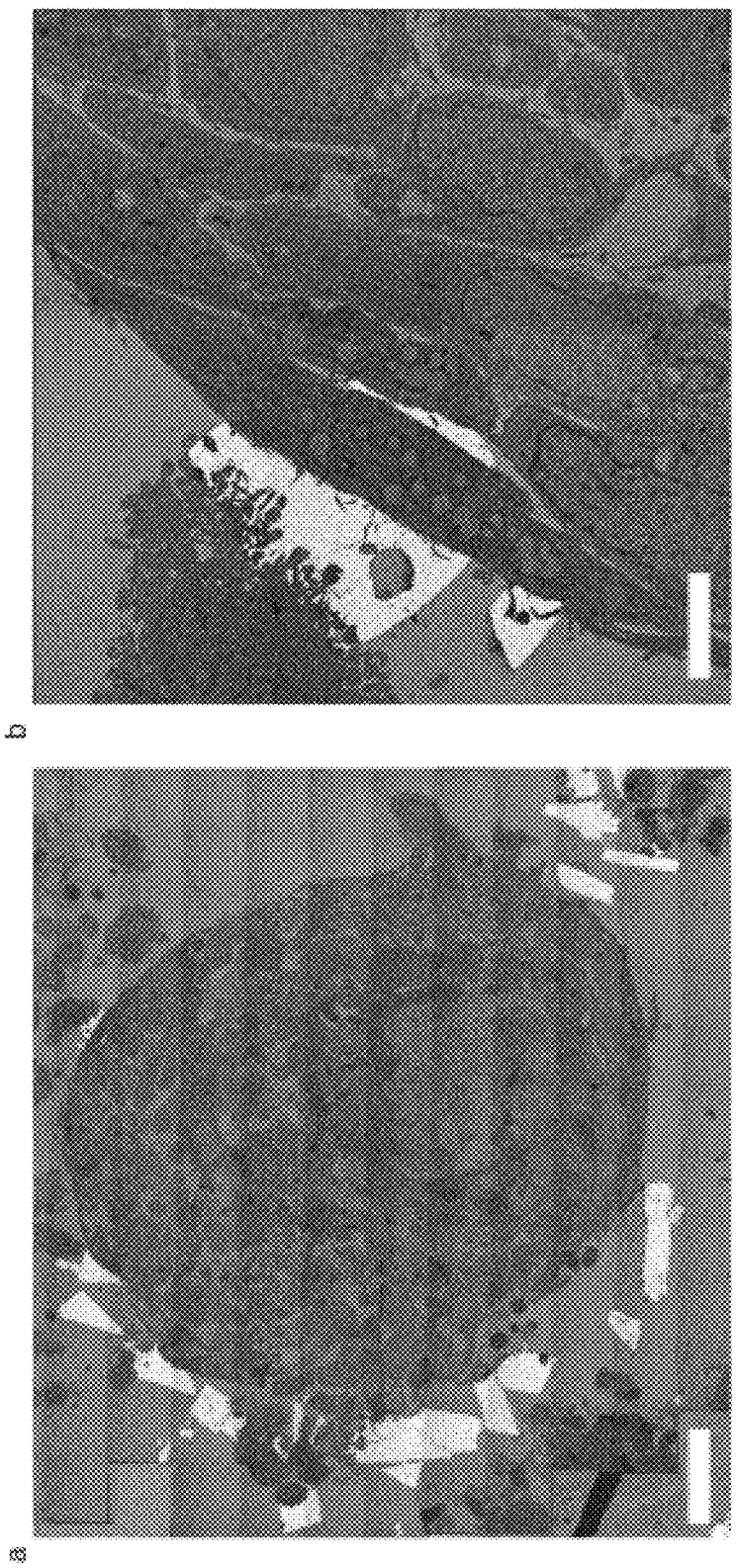
FIG. 19 shows transmission electron microscopy imaging of the ps-plaque. (a) TEM image of a ps-plaque showing accumulation of structured cholesterol crystals at the external plaque surface. Scale bar 40 μm. (b) Detail of the ps-plaque external surface. Apoptotic myofibroblast in contact with a structured cholesterol crystal. Scale bar 4 μm.
Figure 21:
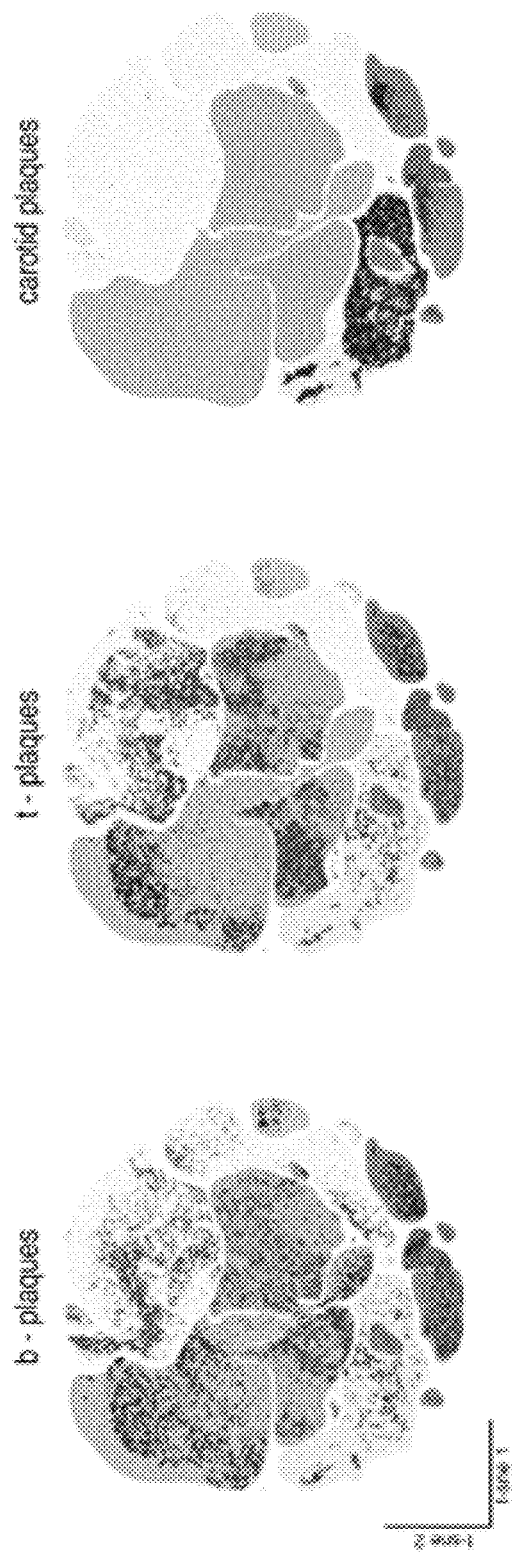
FIG. 21 shows a comparison between biofabricated plaques and human carotid plaques: vi-SNE maps from CD45+ populations isolated from blood-derived plaques (b-plaques), thp1 plaques (t-plaques) and carotid plaques.
Figure 22:
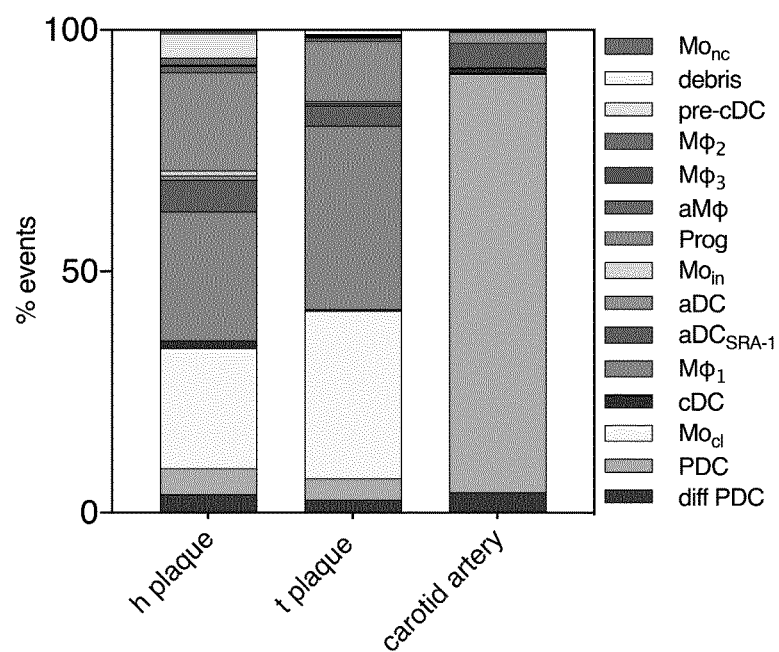
FIG. 22 shows a comparison between biofabricated plaques and human carotid plaques: The stacked-bar chart summarizes the percentage of events for each population.

Example 4: vi-SNE Analysis Reveals Plasmacytoid and Activated Dendritic Cells as Main Myeloid Components in Human Fibroatheroma To corroborate the ps-plaque model the inventors conducted a comparison study between bioengineered and human atherosclerotic plaques isolated from patients that underwent carotid endarterectomy. First, they sorted CD45+ populations from bioengineered blood-derived ps-plaques (b-plaques), thp1-derived ps-plaques (t-plaques) and human carotid plaques. Second, they analysed and compared the population distribution within the samples using flow cytometry. The inventors observed large similarities in population distribution within b-plaques and t-plaques. In detail, they found that the main cell populations are classical monocytes, macrophages, activated dendritic cells and plasmacytoid dendritic cells (FIG. 2$a,b$; FIG. 8). When they analysed CD45+ cells from carotid plaques, they identified PDC and aDC populations as main myeloid plaque components (FIG. 21, FIG. 22; FIG. 9). The inventors further investigated the event density distribution within the PDC populations in human carotid plaques. The inventors identified 3 major areas of the vi-SNE map corresponding to peculiar PDC phenotypes that they classified as α, β and γ (FIG. 9). PDC type-α represents a relatively small cluster with phagocytic and lipoprotein clearance predisposition due to high surface levels of scavenger receptors CD36, SRA-1 and CD14. PDC type-δ is a larger cell cluster characterized by CD16high, indicating a possible involvement in pro-inflammatory reactions. PDC type-γ appears to be exclusively specialized in lipid and lipoprotein uptake, provided the predominant surface expression levels of CD36 (FIG. 9). Interestingly, in both bioengineered plaque models (b- and t-plaques) the inventors identified PDC Type-8 (FIG. 8). Finally, they analysed the gene expression profile of the CD45+ populations in ps-plaques and carotid plaques. The inventors reported a significant down-regulation of pro-inflammatory and remodelling gene targets in carotid plaques compared to bioengineered plaques (FIG. 16$a$-$b$).

Figure 10:
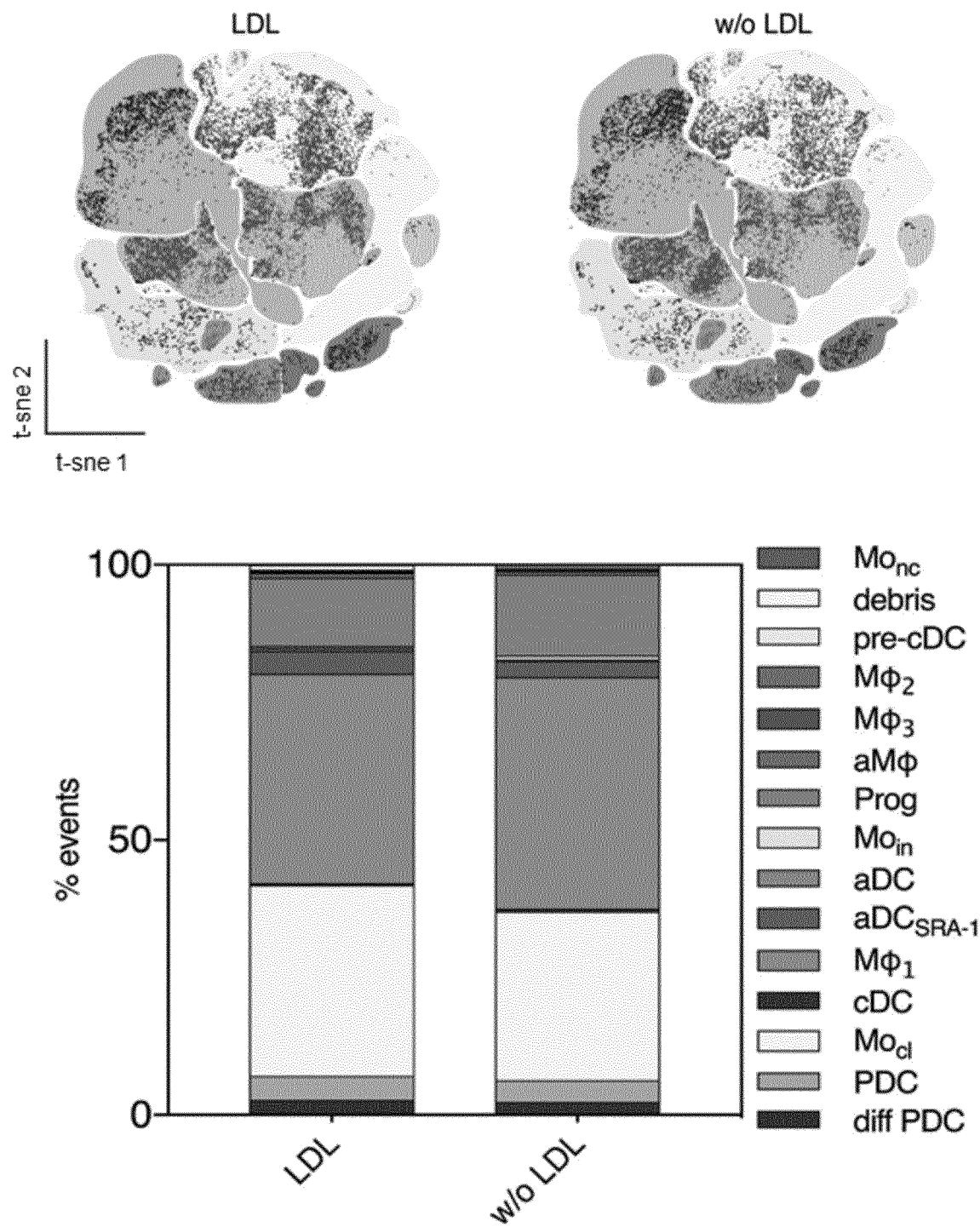
FIG. 10 shows LDL effects on t-plaque myeloid populations. vi-SNE maps indicating different myeloid populations identified in LDL-rich (LDL) or LDL-free (w/o LDL) t-plaques. The part-of-whole graph summarizes the results depicted in the vi-SNE maps. n=7; 2,000 events per sample are reported for a total of 14,000 events in each vi-SNE map.
Figure 11:
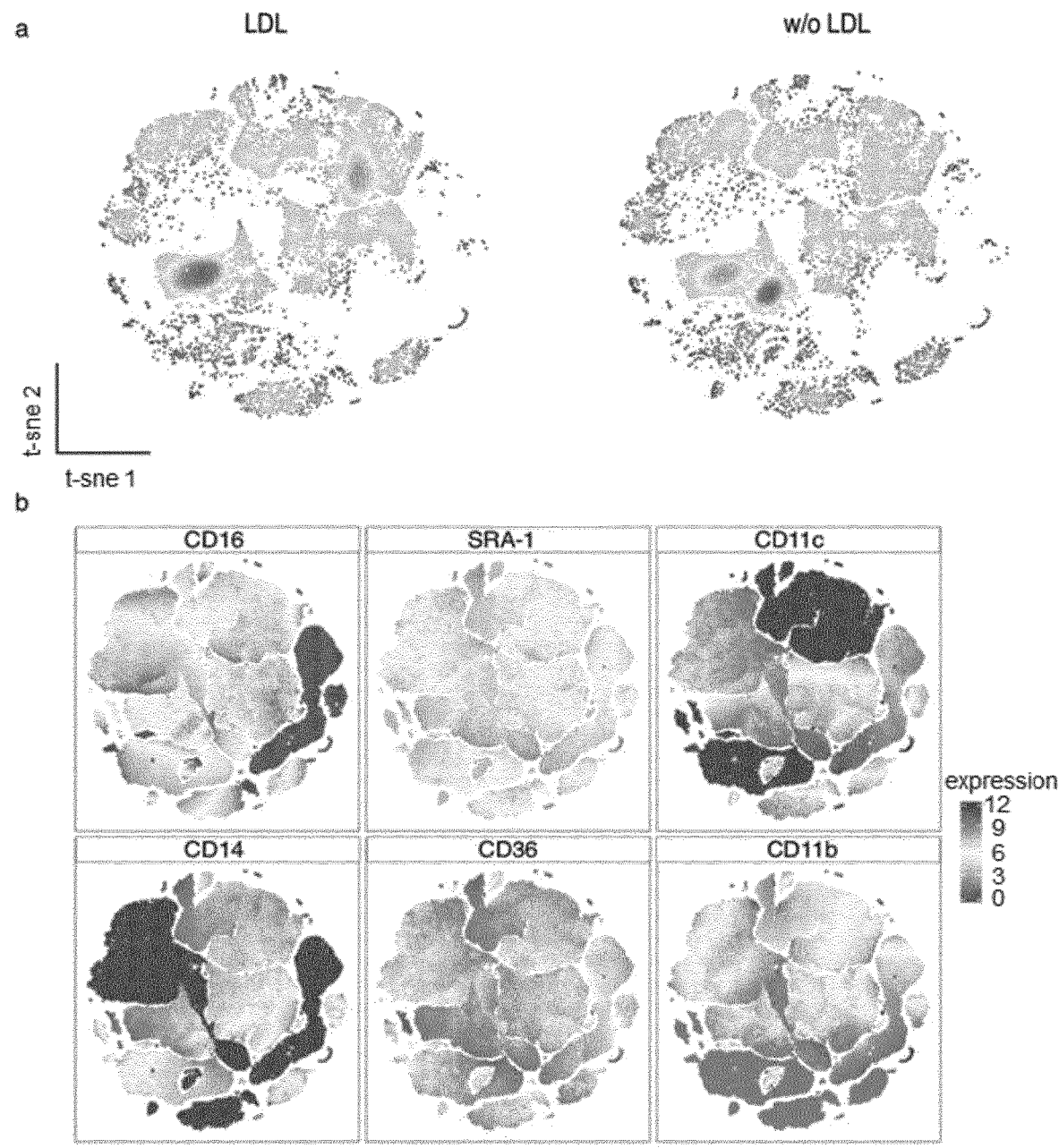
FIG. 11 shows LDL effects on myeloid populations isolated from t-plaques. (a) Event density maps of myeloid populations from LDL-rich (LDL) or LDL-free (w/o LDL) t-plaques. High-density (red) and low-density (blue) areas are shown. n=7; 2,000 events per sample are reported. 14,000 events are displayed in each vi-SNE map. (b) Marker expression level plots.
Figure 23:
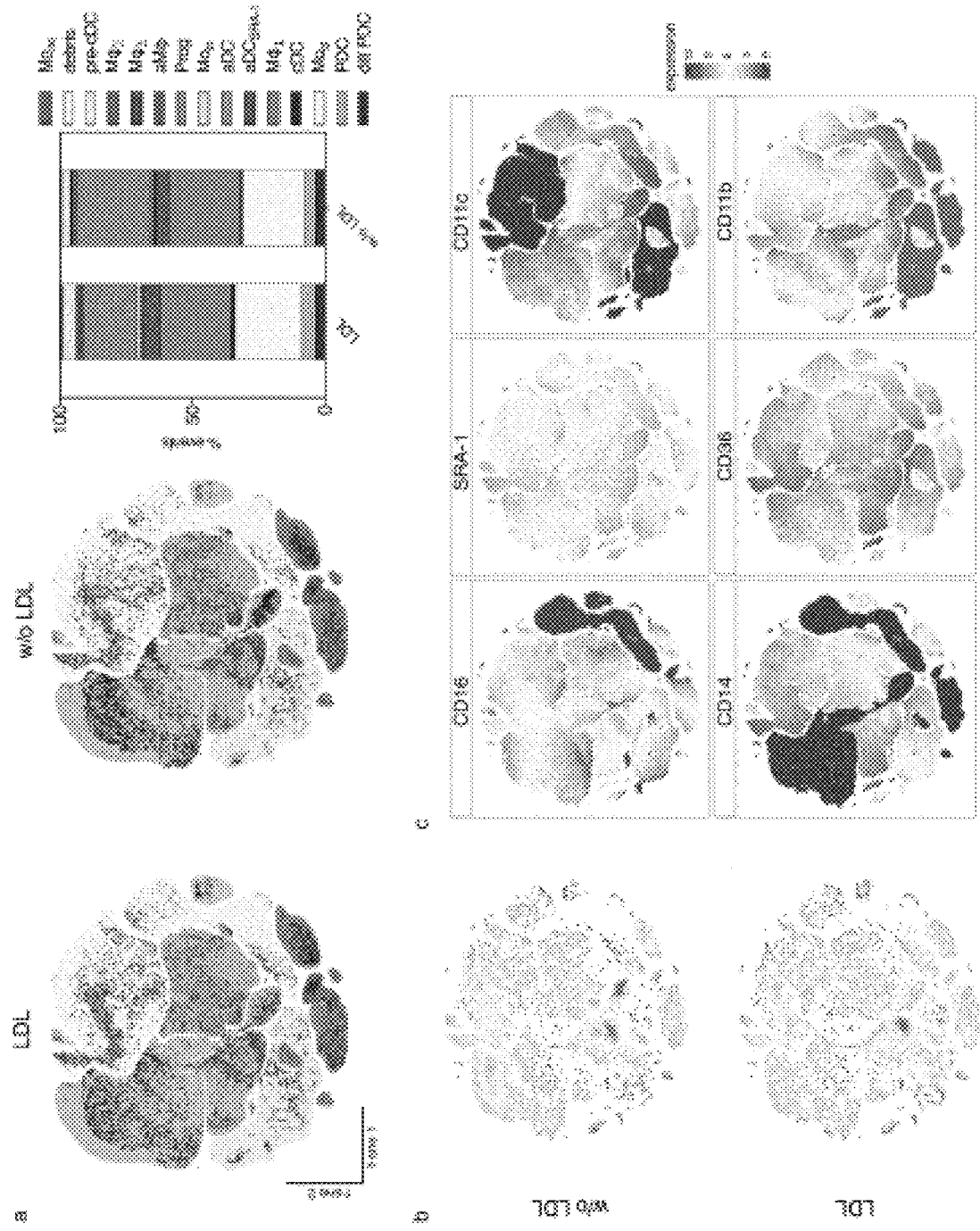
FIG. 23 shows LDL effects on myeloid cells isolated from b-plaques. (a) vi-SNE maps indicating myeloid populations identified within b-plaques biofabricated either using LDL-enriched (LDL) or LDL-free (w/o LDL) medium. The stacked-bar chart summarizes the results from the vi-SNE maps and reports the percentage of events recorded in each population. (b) Event density distribution vi-SNE maps show high-density (red) and low-density of events (blue) areas. (c) Marker expression level vi-SNE plots.

Example 5: Low-Density Lipoprotein Promotes the Differentiation of a Precursor Myeloid Population in Biofabricated Plaques The inventors investigated the effects of LDL on the differentiation of myeloid (CD45+) subpopulations isolated from b- and t-plaques. To do so, they biofabricated ps-plaques using either the established protocol based on LDL-enriched medium or using LDL-free medium. They applied the vi-SNE workflow to compare the respective cell populations. In b-plaques they observed a reduced count of precursors in LDL-enriched versus LDL-free controls (p<0.001, FIG. 23$a$) suggesting differentiation triggered by LDL. The difference in precursor counts can also be appreciated in the respective density plots (FIG. 23$b$). Additionally, they compared vi-SNE density plots from ps-plaques biofabricated in LDL-rich and LDL-free medium. To investigate variations in LDL triggered surface antigen expression within each population they overlapped the density plots with the marker expression level plot. The inventors observed an LDL dependent density shift in aDC towards vi-SNE areas with CDllchigh, CD16high and CD36high expression levels (FIG. 23$b,c$). In t-plaques, they observed an LDL dependent density shift of Mφ1 towards CD36high and CDllchigh areas of the vi-SNE map and of Mocl towards a CD36high vi-SNE area (FIG. 10; FIG. 11).

Figure 12:
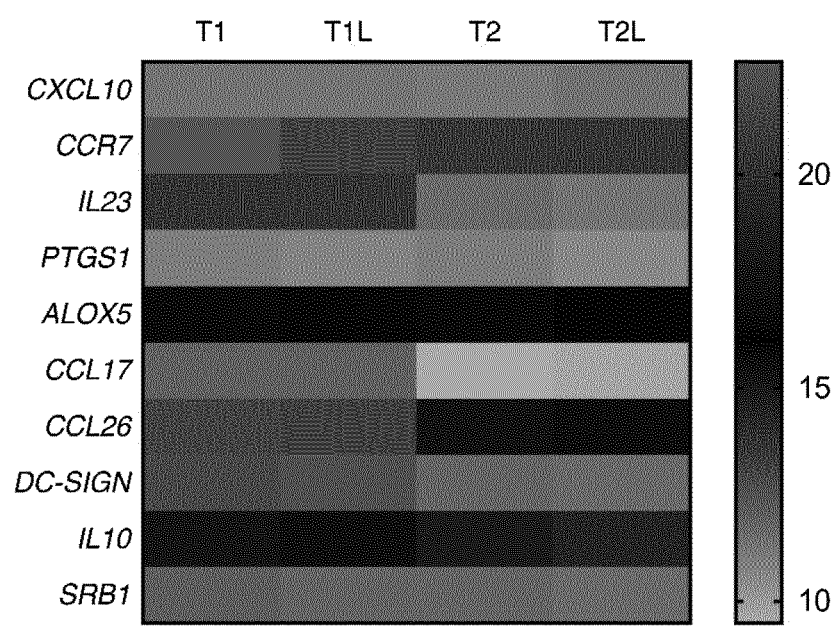
FIG. 12 shows the variation in gene expression profiles during t-plaque formation Heat-map indicating the expression levels of target genes of interest at T1 and T2 of t-plaque formation. Ps-plaques were biofabricated either in LDL-rich (T1L, T2L) or LDL-free (T1, T2) environment. Expression levels are reported in ΔCt over the mean expression of GAPDH and 18S housekeeping genes; n=5.
Figure 24:
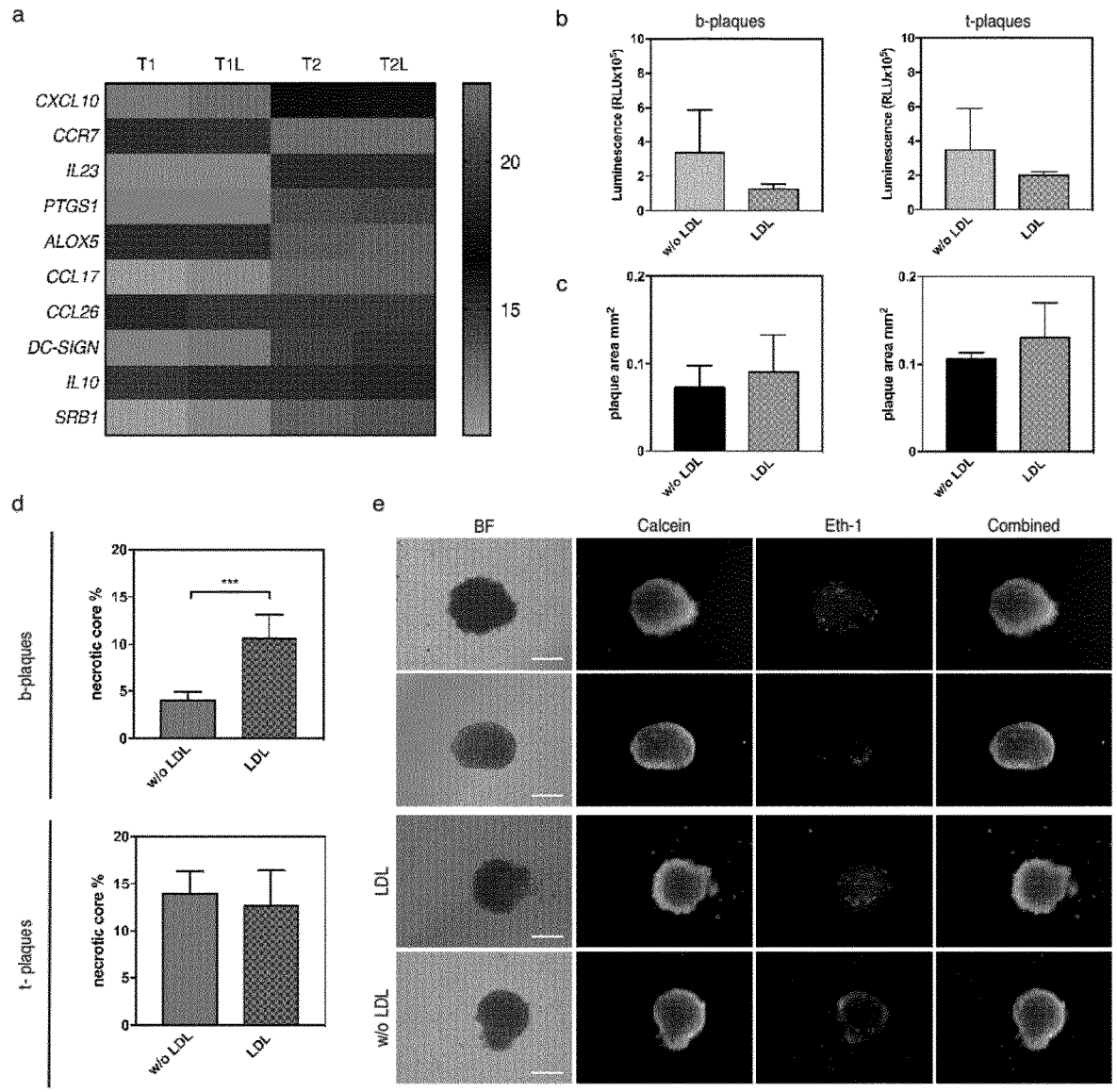
FIG. 24 shows a transcript analysis of pro- and anti-inflammatory gene targets in b-plaques and LDL effects on cell viability and plaque dimension. (a) Heat-map indicating the expression levels of target genes of interest at T1 and T2 of b-plaque formation in LDL presence (T1L, T2L) or absence (T1, T2). Expression levels are reported in ΔCt over the mean of the housekeeping genes GAPDH and 18S; n=5 (b) ATP levels, indicated in relative luminescence units (RLU), were measured and compared in b- and t-plaques; n=5. (c) Plaque circular cross-section area ($mm^2$) as indicator of plaque dimension; n=5. (d-e) The ps-plaque necrotic area was measured at the circular cross-section at the great circle of the spheroid, and indicated as percentage over alive cells. Living cells (green) are stained with calcein while dead cells (red) with Eth-1.

Example 6: The Hanging-Drop Environment Allows the Establishment of a Pro-Inflammatory Niche To uncover possible transcriptional effects exerted by LDL on key target genes, the inventors investigated the expression profiles of the myeloid component during two steps of the ps-plaque biofabrication: (i) after 48 h in hanging-drop (T1) and (ii) at the end of the hanging-drop process (T2). They compared T1 and T2 from ps-plaques produced in LDL-free or LDL-enriched environments. Surprisingly, despite the induction of dendritic cell-specific intercellular adhesion molecule DC-SIGN (p<0.001 versus p=0.003, FIG. 24$a$) they found any LDL-dependent significant transcriptional change in neither b-plaques nor t-plaques (FIG. 24$a$; FIG. 12). On the other hand, they found that the hanging-drop process had, per se, a major influence on the gene expression levels by directly or indirectly promoting the establishment of a pro-inflammatory environment. In detail, in b-plaques the inventors observed a significant down-regulation of CCL26 (p<0.001) and up-regulation of key pro-inflammatory genes CXCL10, CCR7 and IL23 (p<0.001) during the transition from T1 to T2 and independently from the presence of LDL (FIG. 24$a$). They observed an indirect pro-inflammatory effect in t-plaques, exerted through the down-regulation of the anti-inflammatory cytokines CCL26, MO and CCL17 (p<0.001, FIG. 12).

Example 7: Low-Density Lipoprotein Enhances Cell Death in Ps-Plaques Biofabricated with Primed Blood Cells To further explore the effects of LDL on the ps-plaque model the inventors conducted a bivalent analysis. First, they investigated the cell viability within the ps-plaque. They measured and compared the ATP levels produced by the biofabricated plaques in LDL-enriched and LDL-free medium using a luminescence-based ATP assay. The inventors did not find any significant LDL-dependent differences in ATP levels in either b- or t-plaques (FIG. 24b). However, they observed a general tendency of lower ATP levels in plaques produced in LDL-rich environments. The inventors then measured the necrotic area at the circular cross-section with a calcein-ethidium based cell viability assay. They found that the necrotic area at the cross-section of b-plaques fabricated in presence of LDL was significantly larger in comparison to their LDL-free counterparts, suggesting an LDL-dependent necrotic effect ($p<0.001$, FIG. 24d,e). Second, they investigated differences in plaque dimensions to verify possible effects of LDL on cell proliferation. The inventors used the circular cross-sectional area of the ps-plaque as an indicator of plaque size. They found no difference in circular cross-section area—consequently in size—of LDL-enriched vs LDL-free plaques (FIG. 24c).

DISCUSSION

Figure 13:
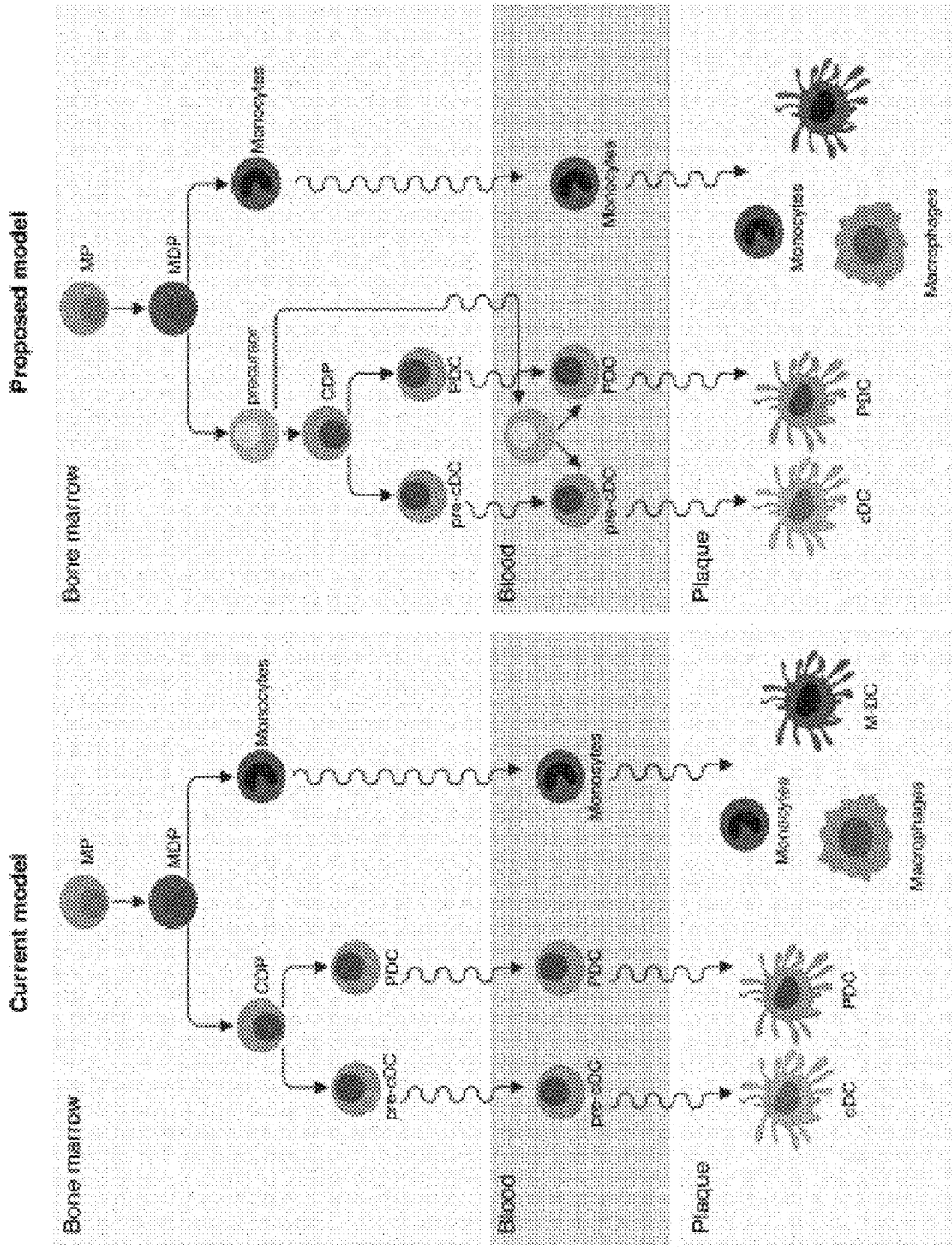
FIG. 13 shows the proposed hematopoietic differentiation model of the myeloid lineage. In the current model of myeloid differentiation, the common macrophage-dendritic cell precursor (MDP) derives from the common myeloid progenitor (MP) and gives rise to monocytes and to the common dendritic cell progenitor (CDP). The latter differentiates in plasmacytoid dendritic cells (PDC) and pre-classical dendritic cells (pre-cDC). Pre-cDC, PDC and monocytes circulate in the blood and can migrate within the plaque where they differentiate in classical dendritic cells (cDC), tissue resident plasmacytoid dendritic cells (PDC), macrophages or monocyte-derived dendritic cells (M-DC). In the proposed model a dendritic progenitor can circulate in the blood and differentiate in pre-cDC and PDC.

With the biofabrication of the ps-plaque the inventors aimed at replicating cellular architecture and extracellular microenvironment of a human atherosclerotic plaque to close an open modelling gap in the field of atherosclerosis research. It has been described that the fibroatheroma cellular composition is mainly characterized by macrophages and dendritic cells retaining pro-inflammatory and remodelling abilities. To achieve plaque cell populations as similar as possible to human atherosclerotic plaque phenotypes, the inventors established a differentiation-priming protocol based on a mild LPS stimulation of cultured adhesive myeloid cells. To visualize and quantify the effects of this procedure on cell population remodelling they used the vi-SNE workflow. With this strategy they identified a total of 15 cell populations, differently distributed among samples. The inventors were able to classify these populations according to the prevalence of specific surface markers. They were also able to track intra-population density shifts and changes in numbers of events. The sensitivity of the vi-SNE analysis allowed the identification of under-represented myeloid populations, otherwise difficult to identify with commonly used flow cytometry analysis tools. Thanks to the vi-SNE workflow the inventors identified in blood-derived myeloid samples both plasmacytoid dendritic cells (PDC) and pre-classical dendritic cells (pre-cDCs). Interestingly, although thp-1 cells and blood-derived myeloid populations share remarkable similarities concerning population distribution, PDC are almost absent from thp-1 samples before the differentiation-priming treatment, emphasizing the differences between the thp-1 cell line and their physiological counterparts previously discussed by Bosshart and Heinzelmann. Moreover, the vi-SNE analysis reported a yet unidentified myeloid population in both thp-1 and blood derived samples. The inventors observed a significant decrease of this population upon differentiation-priming treatment in both blood-derived and thp-1 samples. The decrease was concomitant to a significant increase in pre-cDC count in blood-derived samples and to an increase in PDC in thp-1 samples. Based on the current myeloid differentiation map and on their observations the inventors propose that the yet unidentified population could be classified as a circulating common precursor of pre-cDC and PDC, differentiating from the common dendritic cell precursors located in the bone marrow (FIG. 13). Further investigation on this cell population could improve understanding and redesigning of the myeloid differentiation map. Primed cells and myofibroblasts were used for ps-plaque biofabrication and helped to generate a stratified cell-spheroid with myofibroblasts located at the periphery and a compact, collagenous and lipid-rich core of CD45+ cells. The inventors sorted and compared the CD45+ populations derived from ps-plaques and native human carotid plaques using the vi-SNE workflow. They found that PDC and activated dendritic cells (aDC) are the main plaque myeloid component of thin-cap stage atherosclerotic plaque. This finding is per se surprising provided that macrophages and macrophage-derived foam cells are thought to be the main cellular component of atherosclerotic lesions, at least in early developmental stages, as discussed by Moore et al., Cell, 2011, and Randolph et al., Circ Res, 2014. Bonanno et al., Cyometry, 2000, previously analysed the cell component of human carotid plaques using flow cytometry showing that about 17% of the lesion (considering cells of lymphoid and myeloid origin and smooth muscle cells) was constituted by CD68+ cells. The inventors also reported that about 40% of the cells within the plaque expressed MHC class II molecules (HLA-DR+) suggesting that they could act as antigen-presenting cells. It was also proven that early-committed immature DCs are positive for CD68 and HLA-DR markers supporting the idea that the cells analysed by Bonanno et al., Cyometry, 2000, might have been in part PDC and activated dendritic cells. Additionally, it is known that PDC aggravate atherosclerotic lesion formation and their depletion reduces aortic plaque growth by 46% in $Apoe^{-/-}$ mice. PDC are also able to uptake oxidized LDL (ox-LDL) ex vivo, and promote PDC-driven antigen-specific T-cell proliferation. Finally, it was reported that PDC function and cytokine release is impaired in patients suffering from coronary artery disease. Taken together, these discoveries are in line with our findings and might change the scenario of future atherosclerosis treatments. Within the PDC population the inventors identified 3 overrepresented sub-populations that they named type-$\alpha$, type-$\beta$ and type-$\gamma$. The inventors observed that these subpopulations retain some degree of specialization due to differential marker expression levels. This difference could be the basis of a differential contribution to plaque maturation. For instance, PDC type-$\alpha$ display surface marker expression levels ($CD36^{high}$, $CD14^{high}$ and $SRA-1^{high}$) of a specialized scavenger population. With the ps-plaque model the inventors were able to investigate LDL effects on intra-plaque population remodelling and cell viability. In detail, they monitored LDL-dependent event density shift within the PDC population towards PDC type-$\beta$ phenotype. This shift was not concomitant with the increase in the PDC count implying a PDC polarization towards CD36high and CD16high vi-SNE regions and indicating a possible LDL-triggered acquisition from PDC of scavenger and pro-inflammatory phenotype. Additionally, the inventors found that LDL presence during ps-plaque formation significantly decreased the count of dendritic precursors in both b- and t-plaques and triggered the polarization of aDCs towards $CD11c^{high}$ $CD16^{high}$ and $CD36^{high}$ levels. These findings are supported by the previous observations that LDL and mildly oxidized LDL affect DC maturation and promote pro-inflammatory function. Moreover, the inventors observed an LDL-dependent decrease of plaque cell viability in b-plaques but not in t-plaques. It was shown that LDL and ox-LDL accumulate in the cytoplasm of the phagocyte and ultimately contribute to a deregulation of lipid metabolism by activating the unfolded protein response (UPR), leading to cell death. The non-significant decrease in cell viability observed in t-plaques might be due to intrinsic differences in population counts among ps-plaque types. In fact, t-plaques show higher intermediate monocyte counts when compared to b-plaques. Furthermore, b-plaques display a larger population of activated dendritic cells compared to t-plaques. In summary, t-plaques are constituted by a more immature cellular milieu compared to b-plaques. For this reason the inventors hypothesize that populations within t-plaques would require more time to develop towards a death-susceptible stage in presence of LDL. Finally, the inventors investigated time-dependent effects of LDL on the expression profile of myeloid cells within the plaque. They found no significant difference in transcript levels of selected pro-inflammatory and remodelling target genes comparing LDL-rich and LDL-free plaques. LDL effects on myeloid cell transcriptome were previously investigated by exposing the cells directly in contact with modified forms of LDL and not by directly testing native lipoproteins. Though the latter might retain slower time of action at the transcriptomic level compared to its modified counterparts, as previously observed on human smooth muscle cells. Interestingly, the inventors detected time-dependent gene induction leading to pro-inflammatory cell phenotype independent to LDL treatment. The latter was either prompted by direct up-regulation of pro-inflammatory target genes in b-plaques (CXCL10, CCR7, IL23, PTGS1) or indirectly triggered by down-regulation of anti-inflammatory genes in t-plaques (CCL17, CCL26, IL10). It was recently shown that three-dimensional spheroid cultures of adipose-derived mesenchymal stem cells (MSC) enhance protein levels of the anti-inflammatory tumor necrosis factor-alpha stimulated gene/protein 6 (TGS-6). On the other hand, the study conducted by Bartosh et al., Proc Natl Acad Sci USA, 2010, did not include any test to verify the possible concomitant release of pro-inflammatory proteins, leaving an unanswered question open for further investigations. In conclusion, the ps-plaque is assembled with myeloid cell populations that are shared with human native plaques. These cells are embedded in a collagenous and lipid-rich extracellular matrix surrounded by a fibrotic layer. To the inventors' knowledge the ps-plaque can be considered the in vitro model closer to human fibroatheroma available up to date.

TABLE 1

Myeloid populations in ps-plaques and native carotid plaques.

| Plaque components | | Abbreviation | % b-plaque | % total | % t-plaque | % total | % nat. plaque | % total |
|---|---|---|---|---|---|---|---|---|
| Monocytes | Classical | Mocl | 24.92 | 26.31 | 34.64 | 35.14 | 0.2 | 0.23 |
| | Intermediate | Moin | 0.97 | | 0.44 | | 0.03 | |
| | Non classical | Monc | 0.42 | | 0.06 | | 0.00 | |
| Macrophages | Derived from MOcl | MΦ1 | 26.66 | 29.59 | 38.06 | 39.18 | 0.04 | 0.23 |
| | Derived from MOcl | MΦ2 | 1.38 | | 0.11 | | 0.00 | |
| | Derived from MOin | MΦ3 | 0.27 | | 0.21 | | 0.05 | |
| | Activated | aMΦ | 1.28 | | 0.8 | | 0.14 | |
| Dendritic cells | Plamacytoid | PDC | 5.37 | 43.83 | 4.37 | 24.86 | 86.68 | 99.54 |
| | Differentiated PDC | Diff PDC | 3.85 | | 2.76 | | 4.21 | |
| | Pre-classical | Pre-cDC | 5.12 | | 0.31 | | 0.06 | |
| | Classical | cDC | 1.6 | | 0.42 | | 1.01 | |
| | Activated | aDC | 0.93 | | 0.40 | | 2.27 | |
| | Activated SRA-1$^{high}$ | aDCSRA-1 | 6.58 | | 4.18 | | 5.15 | |
| | Progenitors | Prog | 20.38 | | 12.42 | | 0.16 | |
| | | debris | 0.27 | | 0.82 | | 0.00 | 0.00 |

List 1 shows primers. Gene of interest, forward (FW) and reverse (RV) primer sequences are listed.

```
SEQ ID NO 01: CXCL10 for
GCA AGC CAA TD TGT CCA CG

SEQ ID NO 02: CXCL10 rev
ACA DT CCT TGC TAA CTG CD TCA G

SEQ ID NO 03: CCR7 for
GAAAGT CCA GAAACT GD CCC ACC TGC

SEQ ID NO 04: CCR7 rev
CCC CTC TGA AGA ACC GAA CCA CTC CD

SEQ ID NO 05: CCL17 for
CCA GGG ATG CCA TCG TD DG TAA CTG TGC

SEQ ID NO 06: CCL17 rev
CCT CAC TGT CCC TCT TCT TCG TCC CTG GAA

SEQ ID NO 07: CCL26 for
GCC TGA DT GCA GCA TCA TGA TGG

SEQ ID NO 08: CCL26 rev
CGG ATG ACA AD CAG CTG AGT CAC

SEQ ID NO 09: DC-SIGN for
TCG AGG ATA CAA GAG CD AGC A

SEQ ID NO 10: DC-SIGN rev
AAG GAG CCC AGC CAA GAG

SEQ ID NO 11: IL10 for
CTG TGAAAA CAA GAG CAA CCC

SEQ ID NO 12: IL10 rev
GAA GCT TCT GD CCC TCC C

SEQ ID NO 13: IL23 for
GCA GAT TCC AAG CCT CAG TC

SEQ ID NO 14: IL23 rev
DC AAC ATA TGC AGG TCC CA

SEQ ID NO 15: PTGS1 for
CCC CAG TGAATC CCT GD GD
```

-continued

SEQ ID NO 16: PTGS1 rev
AAG GTG GCA DG ACAAAC TCC

SEQ ID NO 17: ALOX5 for
CCC CGA CD TGA GAA AAT CT

SEQ ID NO 18: ALOX5 rev
GGC TGC ACT CTA CCA TCT CC

SEQ ID NO 19: SRB1 for
TCC TCA CD CCT CAA CCC TG

-continued

SEQ ID NO 20: SRB1 rev
TCC CAG TD GTC CAA TGC C

SEQ ID NO 21: GAPDH for
GTC ACT GGT GGA CCT GAC CT

SEQ ID NO 22: GAPDH rev
ACC TGG TGC TCA GTG TAG CC

SEQ ID NO 23: 18S for
CCC GGG GAG GTA GTG ACG AAAAAT

SEQ ID NO 24: 18S rev
GCC CGC TCC CAA GAT CCAACT AC

---

The invention claimed is:

1. An in vitro engineered layered cellular aggregate, comprising;
   an inner sphere consisting essentially of plurality of myeloid cells, collagen, and cholesterol, and
   an outer lining consisting essentially of fibroblasts, wherein said outer lining encases said inner sphere, and wherein said cellular aggregate has a diameter of 100 µm-500 µm and does not contain a pre-formed, cell-free scaffold.

2. The in vitro engineered cellular aggregate according to claim 1, wherein said plurality of myeloid cells comprises monocytes, macrophages and dendritic cells.

3. The in vitro engineered cellular aggregate according to claim 2, wherein said monocytes, macrophages and dendritic cells are each present at a defined ratio, wherein said defined ratio is
   20%-40%, 26%-36%, or 31% of monocytes;
   25%-45%, 29%-39%, or 34% of macrophages; and
   15%-45%, 20%-40%, or 31% of dendritic cells.

4. The in vitro engineered cellular aggregate according to claim 1, wherein said plurality of myeloid cells is positive for the expression of a proinflammatory marker selected from the group consisting of CXCL10, CCR7, IL23, PTGS1 and ALOX5.

5. The in vitro engineered cellular aggregate according to claim 1, wherein said plurality of myeloid cells is positive for the expression of a remodelling marker selected from the group consisting of CCL17, CCL26, DC-SIGN, IL10 and SRB1.

6. A plurality of the layered cellular aggregates according to claim 1, wherein the plurality of the layered cellular aggregates is integrated in a 96 or 384-well platform.

7. The in vitro engineered layered cellular aggregate, according to claim 1 wherein the collagen is collagen III.

8. A method for the generation of the engineered layered cellular aggregate of claim 1, comprising the steps of;
   a) providing a population of myeloid cells, wherein said myeloid cells are provided
      (i) ex-vivo from a patient by isolation from fresh blood using a double gradient centrifugation; or
      (ii) ex vivo as cell culture or cell line characterized by expression of monocyte/macrophage cell markers;
   b) in a differentiation-priming step, contacting said myeloid cells with a protein kinase C agonist, yielding primed myeloid cells;
   c) in a culture step, incubating said primed myeloid cells in the presence of low-density lipoprotein (LDL) in a confined volume in a hanging drop culture; yielding a 3-dimensional culture, a sphere of myeloid cells; and
   d) in a co-culture step, incubating said 3-dimensional culture of myeloid cells together with fibroblasts in a confined volume, in a hanging drop culture in the presence of LDL, yielding said layered cellular aggregate.

9. The method according to claim 8, wherein said protein kinase C agonist is a phorbol ester, or phorbol 12-myristate 13-acetate (PMA).

10. The method according to claim 8, wherein in said differentiation-priming step, said myeloid cells are contacted with 5-200 ng/ml PMA, with 5-50 ng/ml PMA, or with 10 ng/ml PMA, and for 36-120 hours, for 48-96 hours, or for 72 hours.

11. The method according to claim 8, wherein subsequently to said differentiation-priming step, said primed myeloid cells are contacted with lipopolysaccharide (LPS).

12. The method according to claim 11, wherein subsequently to said differentiation-priming step, primed myeloid cells are contacted with 10-100 ng/ml LPS for 30 min-3 hours, or with 10 ng/ml LPS for 1 hour.

13. The method according to claim 8, wherein said myeloid cells are human myeloid cells.

14. The method according to claim 8, wherein said fibroblasts are human fibroblasts.

* * * * *